United States Patent
Chen

(10) Patent No.: US 8,329,688 B2
(45) Date of Patent: Dec. 11, 2012

(54) TRANS-4-[[(5S)-5-[[[3,5-BIS(TRIFLUORO-METHYL)PHENYL]METHYL](2-METHYL-2H-TETRAZOL-5-YL)AMINO]-2,3,4,5-TETRAHYDRO-7,9-DIMETHYL-1H-1-BENZAZEPIN-1-YL]METHYL]-CYCLOHEXANECARBOXYLIC ACID

(75) Inventor: Xinchao Chen, Schenectady, NY (US)

(73) Assignee: Eli Lilly and Company, Indianapolis, IN (US)

( * ) Notice: Subject to any disclaimer, the term of this patent is extended or adjusted under 35 U.S.C. 154(b) by 262 days.

(21) Appl. No.: 12/824,355

(22) Filed: Jun. 28, 2010

(65) Prior Publication Data

US 2010/0331309 A1    Dec. 30, 2010

Related U.S. Application Data

(60) Provisional application No. 61/221,708, filed on Jun. 30, 2009.

(51) Int. Cl.
*A61P 9/10* (2006.01)
*A61K 31/55* (2006.01)
*C07D 403/12* (2006.01)

(52) U.S. Cl. .................................. 514/213.01; 540/593
(58) Field of Classification Search .............. 514/213.01; 540/593
See application file for complete search history.

(56) References Cited

U.S. PATENT DOCUMENTS

| | | | |
|---|---|---|---|
| 6,140,343 A | 10/2000 | DeNinno et al. | |
| 6,147,089 A | 11/2000 | DeNinno et al. | |
| 6,197,786 B1 | 3/2001 | DeNinno et al. | |
| 6,313,142 B1 | 11/2001 | Damon et al. | |
| 6,489,478 B1 | 12/2002 | DeNinno et al. | |
| 6,689,897 B2 | 2/2004 | Damon et al. | |
| 7,749,992 B2 * | 7/2010 | Cao et al. .................. | 514/213.01 |
| 7,786,108 B2 | 8/2010 | Chen et al. | |
| 2004/0082609 A1 | 4/2004 | Ghosh et al. | |
| 2004/0204450 A1 | 10/2004 | Bechle et al. | |
| 2005/0059810 A1 | 3/2005 | Maeda et al. | |
| 2006/0100239 A1 | 5/2006 | Nagasaki et al. | |
| 2006/0135551 A1 | 6/2006 | Baruah et al. | |
| 2010/0204207 A1 * | 8/2010 | Chen et al. .................... | 514/215 |
| 2012/0058990 A1 * | 3/2012 | Chen et al. ............... | 514/213.01 |

FOREIGN PATENT DOCUMENTS

| | | |
|---|---|---|
| WO | 0140190 | 6/2001 |
| WO | 2005037796 | 4/2005 |
| WO | 2005097805 | 10/2005 |
| WO | 2005097806 | 10/2005 |
| WO | 2006002342 | 1/2006 |
| WO | 2006012093 | 2/2006 |

OTHER PUBLICATIONS

Second Preliminary Amendment submitted in U.S. Appl. No. 12/763,344, filed Apr. 1, 2011.
Ishihara, et al., "A New Chiral BLA Promoter for Asymmetric Aza Diels-Alder and Aldol-Type Reactions of Imines," J. Am. Chem. Soc., vol. 116, pp. 10520-10524 (1994).
Fuchigami, et al., "Cationic Polar Cycloaddition with Anodically Prepared a-TRI- and a-Difluoromethylated N,Q-Acetals: Preparation of Fluoro-Methylated Tetra-and Dihydroquinoline Derivatives," Heterocycles, vol. 31, No. 3, p. 415 (1990).
Ishitani, et al., "Catalytic Asymmetric Aza Diels-Alder Reactions Using a Chiral Lanthanide Lewis Acid. Entantioselective Synthesis of Tetrahydroquinoline Derivatives Using a Catalytic Amount of a Chiral Source," Tetrahedron Lett., vol. 37, No. 41, pp. 7357-7360 (1996).
Prato, et al., "Evidence of a Two-Step Ionic Mechanism in the Addition of Aromatic Schiff Bases to Enol Ethers," Gazzetta Chimica Italinan, vol. 118, pp. 797-798 (1988).
Guckian, et al., "Design and synthesis of a series of meta aniline-based LFA-1 ICAM inhibitors," Bioorganic & Medicinal Chemistry Letter, vol. 18, pp. 5249-5251 (2008).
Fritsch, et al., "Syntheses, Enrichment of Enantiomers, and Barriers to Racemization of Twisted 9,10-Phenanthrenequinones," Chem. Ber., vol. 125, pp. 849-855 (1992).
Houpis, et al., "Towards the Synthesis of HIV-Protease Inhibitors. Synthesis of Optically Pure 3-Carboxyldecahydroisoquinolines," Tetrahedron Letters, vol. 34, No. 16, pp. 2593-2596 (1993).
Rejection Dated Nov. 30, 2011.
Response to Rejection Dated Feb. 29, 2012.
Final Rejection Dated Apr. 6, 2012.
Preliminary Amendment Dated Nov. 4, 2011.
Preliminary Amendment Dated Nov. 11, 2011.
Preliminary Amendment Dated May 4, 2012.
Response dated Jul. 27, 2012.

* cited by examiner

*Primary Examiner* — Brenda Coleman
(74) *Attorney, Agent, or Firm* — James B. Myers

(57) ABSTRACT

Compounds of a formula

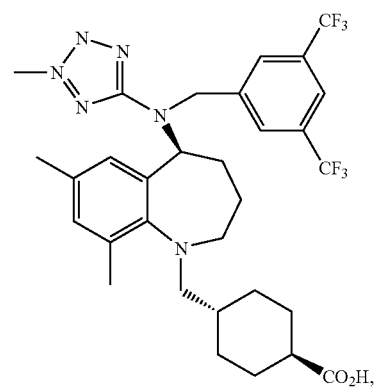

entitled, trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid, as a free acid or a pharmaceutically acceptable salt thereof; and hydrates and other solvates in crystalline form; pharmaceutical formulations; and methods of use are disclosed.

1 Claim, No Drawings

TRANS-4-[[(5S)-5-[[[3,5-BIS(TRIFLUORO-METHYL)PHENYL]METHYL](2-METHYL-2H-TETRAZOL-5-YL)AMINO]-2,3,4,5-TETRAHYDRO-7,9-DIMETHYL-1H-1-BENZAZEPIN-1-YL]METHYL]-CYCLOHEXANECARBOXYLIC ACID

The present application claims the benefit of U.S. Provisional Application Ser. No. 60/221,708 filed on 30 Jun. 2009, which is hereby incorporated by reference in its entirety.

The current invention relates to trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid, pharmaceutically acceptable salts and crystalline forms of this compound as well as to their preparation and methods of treatment using the compound.

Dyslipidemia is a major risk factor for cardiovascular diseases (CD). Low plasma levels of high density lipoprotein cholesterol (HDL-c) with either normal or elevated levels of low density cholesterol (LDL-c) is a significant risk factor for developing atherosclerosis and associated coronary artery disease. Cholesteryl (or cholesterol) ester transfer protein (CETP) is a glycoprotein that facilitates the exchange of cholesteryl esters in HDL for triglycerides in triglyceride-rich lipoproteins. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

Published PCT application WO 06/002342 discloses certain compounds having the structure below where $R^1$-$R^6$ are described therein which are useful for treating cardiovascular diseases.

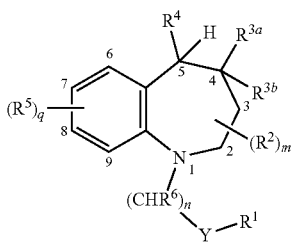

The above disclosure notwithstanding, a great need remains, for effective compounds useful to treat cardiovascular diseases including atherosclerosis and/or dyslipidemia.

There is a need to provide compounds effective to treat cardiovascular disease via oral dosing, which are stable in an acidic environment such as that in the stomach. Further once administered, the compounds need to exhibit sufficiently high bioavailability and/or oral exposure for greater efficacious treatment.

The present invention addresses these needs and provides a compound suitable for treatment of cardiovascular diseases including, but not limited to, dyslipidemia and atherosclerosis. The present invention provides a compound exhibiting particularly advantageous and unexpected properties. The physical and pharmacological properties of the presently claimed compound make it particularly suitable for formulating into tablets for oral dosing. The particular advantageous properties include, among others, greater stability, solubility, and/or bioavailability.

The present invention provides a compound which is trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid, (identified according to its Chemical Abstracts Index Name (referred to herein as BCCA) having the structure of Formula I illustrated below, and pharmaceutically acceptable salts of this compound.

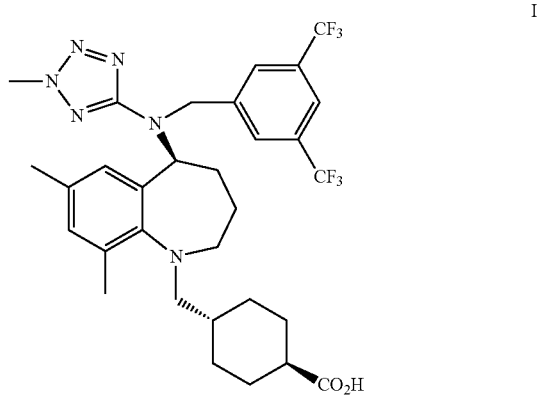

The compound, BCCA, can be a free acid (referred to herein as BCCA free acid), or a pharmaceutically acceptable salt thereof, as a solvate (referred herein as BCCA.solvate) and a hydrate (referred to herein as BCCA.hydrate). The solvate molecules include water (as the hydrate), methanol, ethanol, formic acid, acetic acid, and isopropanol.

The present invention provides a compound which is BCCA, a pharmaceutically acceptable salt thereof, or a hydrate or solvate thereof. In one form the compound BCCA is provided as a free acid, or a pharmaceutically acceptable salt. In other forms, BCCA is provided BCCA.hydrate or BCCA (either as a free acid or salt).solvate in crystalline form. In still other forms, the present invention provides BCCA from BCCA.hydrate or BCCA.solvate to an amorphous solid form.

The present invention provides a compound which is BCCA.hydrate in crystalline form characterized by an X-ray powder diffraction pattern obtained from a CuKα source ($\lambda$=1.54056 Å), which comprises peaks at: a) 7.5, 9.2, 10.7, and 15.5+/−0.2 in 2θ; b) 7.5, 9.2, 10.7, 13.8, 15.0, 15.5, and 19.5+/−0.2 in 2θ; or c) 7.5, 9.2, 10.7, 13.8, 11.3, 15.0, 15.5, 17.7, 19.5, and 25.1+/−0.2 in 2θ.

In another form, the present invention provides a compound which is BCCA.hydrate in crystalline form characterized by a solid state NMR spectrum that comprises peaks referenced to adamantane ($\delta$=29.5 ppm) at: a) 175.6, 168.0 61.1, 21.2, and 18.3+/−0.2 ppm; b) 175.6, 168.0, 145.6, 144.8, 61.1, 45.0, 21.2, and 18.3+/−0.2 ppm; or c) 175.6, 168.0, 145.6, 144.8, 139.9, 136.3, 61.1, 53.0, 49.8, 45.0, 21.2, and 18.2+/−0.2 ppm.

In still other forms, BCCA is provided as BCCA.hydrate in crystalline form as characterized by at least one of the following: a) a X-ray powder diffraction pattern obtained from a CuKα source ($\lambda$=1.54056 Å) which comprises peaks at 7.5, 9.2, 10.7, and 15.5±0.2 in 2θ or b) a solid state NMR spectrum which comprises peaks referenced to adamantane ($\delta$=29.5 ppm) at 175.6, 168.0, 61.1, 21.2, and 18.3+/−0.2 ppm.

The present invention provides a compound which is BCCA.hemi-tert-butylamine salt.hemi ethanol solvate in crystalline form characterized by an X-ray powder diffraction pattern obtained from a CuKα source (λ=1.54056 Å), which comprises peaks at: a) 5.5, 9.0, 14.3, 22.0, and 22.5+/−0.2 in 2θ; or b) 5.5, 9.0, 14.3, 17.5, 18.2, 19.4, 20.6, 22.0, and 22.5+/−0.2 in 2θ; or c) 5.5, 9.0, 13.2, 13.6, 14.3, 15.2, 17.5, 18.2, 19.4, 19.8, 20.6, 22.0, and 22.5+/−0.2 in 2θ.

The present invention provides a compound which is BCCA.formic acid solvate in crystalline form characterized by an X-ray powder diffraction pattern obtained from a CuKα source (λ=1.54056 Å), which comprises peaks at: a) 15.4, 16.9, 18.2, and 18.6+/−0.2 in 2θ; or b) 15.4, 15.7, 16.9, 18.2, 18.6, 19.5, 22.8, 25.7, and 25.5+/−0.2 in 2θ; or c) 13.0, 13.9, 15.4, 15.7, 16.9, 16.4, 18.2, 18.6, 19.5, 20.8, 22.8, 25.7, and 25.5+/−0.2 in 2θ.

The present invention provides a compound which is BCCA.acetic acid solvate in crystalline form characterized by an X-ray powder diffraction pattern obtained from a CuKα source (λ=1.54056 Å), which comprises peaks at: a) 12.9, 15.1, 18.4, 19.4, and 20.8+/−0.2 in 2θ; or b) 12.9, 13.8, 15.1, 16.4, 17.8, 18.4, 19.4, 20.1, and 20.8+/−0.2 in 2θ; or c) 11.00, 12.9, 13.8, 15.1, 15.6, 16.4, 17.8, 18.4, 19.4, 20.1, 20.8, and 21.7+/−0.2 in 2θ.

The present invention provides a compound which is BCCA tert butylamine salt.isopropanol solvate in crystalline form characterized by an X-ray powder diffraction pattern obtained from a CuKα source (λ=1.54056 Å), which comprises peaks at: a) 5.6, 11.3, 12.6, and 17.9+/−0.2 in 2θ; or b) 5.6, 8.0, 11.3, 12.6, 17.9, 20.4, and 24.1+/−0.2 in 2θ.

In another form, the present invention provides a BCCA, or a pharmaceutically acceptable salt thereof, as a solvate where the solvate is selected from: water (also referred to as a hydrate), methanol, ethanol, isopropanol, formic acid, or acetic acid. The BCCA to solvate molar ratio can be from about 1:0.3 to about 1:1, more preferable between about 1:0.5 to about 1:1+/−0.2 (BCCA or salt:solvate). Preferred solvates include water, isopropanol and ethanol.

In another form the present invention provides BCCA as a pharmaceutically acceptable salt. Preferred cations for the pharmaceutically acceptable salt can be selected from: sodium, potassium, magnesium, calcium, zinc, or a tert-butylamine (or tert-butyl ammonium). More preferred cations are sodium, calcium and tert-butylamine.

The present invention provides substantially pure BCCA as BCCA free acid or pharmaceutically acceptable salts thereof, BCCA.hydrate, BCCA.solvate (or BCCA.hydrate) and the BCCA salt.solvate in crystalline form (individually the "referenced BCCA form"). As used herein the term "substantially pure" refers to a composition comprising greater than 80% w/w of the referenced BCCA form, preferable greater than 95% w/w of the referenced BCCA form, and yet more preferable, greater than 98% w/w of referenced BCCA form. In a particularly preferred aspect, the present invention provides substantially pure BCCA.hydrate in crystalline form.

The present invention provides a pharmaceutical composition comprising BCCA, or a pharmaceutically acceptable salt thereof, and at least one of a pharmaceutically acceptable: carrier, excipient or diluent. In selected forms the pharmaceutical composition comprises substantially pure BCCA as BCCA free acid or a pharmaceutically acceptable salt thereof, BCCA.solvate, BCCA salt.solvate or BCCA.hydrate in crystalline form. In a particularly preferred aspect, the pharmaceutical composition comprising substantially pure BCCA.hydrate in crystalline form.

The present invention also provides a method of treating a patient in need thereof, for cardiovascular diseases, in particular arthrosclerosis or dyslipidemia, wherein the method comprises administering an effective amount of BCCA as a free acid, or pharmaceutically acceptable salt, or hydrate thereof to the patient. In preferred forms, the method comprises administering BCCA as BCCA.hydrate.

In still other forms, the present invention provides a method of treating a patient in need thereof, for cardiovascular diseases, in particular arthrosclerosis or dyslipidemia the method comprises administering BCCA.solvate in crystalline form to the patient.

The present invention provides for the use of BCCA (as BCCA free acid or its pharmaceutically acceptable salt, BCCA salt.solvate, BCCA.hydrate, or BCCA.solvate in crystalline form, or BCCA.hydrate in crystalline form) according to the present invention for the manufacture of a medicament for the treatment of cardiovascular diseases including but not limited to dyslipidemia and atherosclerosis.

The present invention provides BCCA (as BCCA free acid; BCCA salt.solvate, BCCA.hydrate, or BCCA.solvate in crystalline form according to the present invention) as a medicament. The present invention also provides BCCA (as BCCA free acid; or BCCA salt.solvate, BCCA.hydrate, BCCA.solvate in crystalline form, in crystalline form according to the present invention) for use in therapy.

The present invention provides BCCA (as BCCA free acid; or BCCA.hydrate, BCCA salt.solvate, or BCCA.solvate in crystalline form according to the present invention) for use in the treatment of cardiovascular diseases including but not limited to dyslipidemia and atherosclerosis.

The present invention also provides a compound having a structure illustrated below:

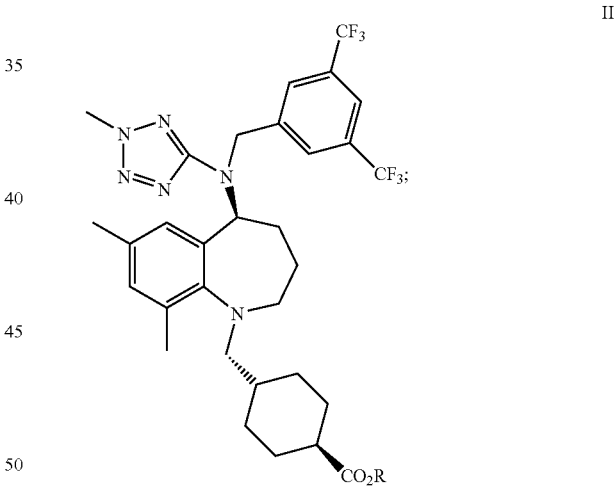

wherein R is selected from a $C_{1-4}$ alkyl, $C_{3-6}$ cycloalkyl, $C_{1-4}$ alkyl-$C_{3-6}$ cycloalkyl, phenyl, and $C_{1-5}$ alkylphenyl to provide a compound of formula I, or a pharmaceutically acceptable salt thereof. Preferred R groups include $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl. Particularly preferred R groups include methyl, ethyl, phenyl and benzyl.

The term $C_{1-4}$ alkyl or $C_{1-5}$ alkyl as referred to herein includes a straight or branched alkyl chain having from 1 to 4 carbon atoms or 1 to 5 carbon atoms, respectively. The term haloalkyl refers an alkyl group having the one or more halogens attached to one or more carbon atoms. As noted above the alkyl group can be a straight or branched chain. Preferred halogens are fluorine, chlorine and bromine Fluorine is particularly preferred.

In still yet another form, the present invention provides a compound which is

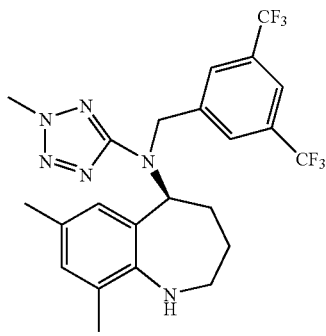

III or a pharmaceutically acceptable salt thereof.

The present invention provides a process for preparing BCCA. The process includes de-esterifying a compound of the formula II below:

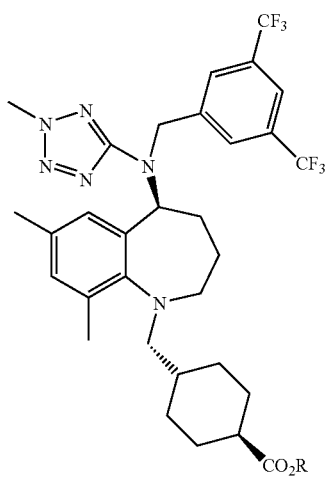

II wherein R is selected from a $C_{1-4}$ alkyl, $C_{1-4}$ haloalkyl, $C_{3-6}$ cycloalkyl, $C_{1-4}$ alkyl-$C_{3-6}$ cycloalkyl, phenyl, or $C_{1-5}$ alkylphenyl to provide a compound of formula I, or a pharmaceutically acceptable salt thereof to provide BCCA or a pharmaceutically acceptable salt thereof. Preferred R groups include $C_{1-4}$ alkyl, phenyl, and $C_{1-5}$ alkylphenyl. Particularly preferred R groups include methyl, ethyl, phenyl and benzyl.

The process can also include deprotecting a protected carboxylic acid substituent on the cyclohexyl group. Examples of various acid protecting functionalities, methods of preparing the protected acids, and methods for deprotecting the acids can be found in "Protecting Groups in Organic Synthesis", 3rd Ed. Greene, T. W., Wuts, P. G. M., Eds., John Wiley and Sons, New York, 1999. It will be recognized by those skilled in the art that in addition to the carboxylic acid and protected carboxylic acid other functional groups that can be readily converted to a carboxylic acid can be used in place the carboxylic acid or protected acid. Such functional groups, preparations, and transformations of these groups to carboxylic acids can be found in "Comprehensive Organic Transformations: A Guide to Functional Group Preparations" by Larock. R. C, Wiley VCH, 1999 and in "March's Advanced Organic Chemistry, Reactions, Mechanisms and Structure" Smith, M. B., and March, J., Wiley-Interscience, 6th Ed. 2007.

In still yet another form, the present invention provides a process as described above and further including condensing a compound of the formula III below

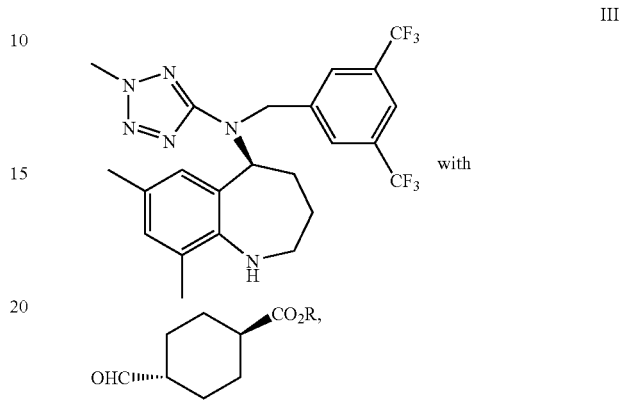

III with where R is as described above, to provide the compound of formula I, or a pharmaceutically acceptable salt thereof. As noted above the carboxylic acid, ester or protected acid illustrated as $CO_2R$ in the structure immediately above can be replaced with a functional group that can be transformed into the carboxylic acid or protected acid.

Preferably an effective CETP inhibitor compound should be stable both chemically and thermally, exhibit sufficient solubility for ease of administration and formulation, and maintain sufficient activity. Furthermore, compounds should exhibit a sufficiently high bioavailability to provide amounts of the compound in vivo for effective treatment. These properties exhibited by BCCA are not taught nor predictable by the prior art.

BCCA.hydrate can be stored at ambient temperature with minor or very little degradation. The compound, BCCA.hydrate in crystalline form has an onset of desolvation and/or melting as measured by differential scanning calorimetry greater than about 50° C., which renders it acceptable for standard industrial processes such as milling. Further, BCCA, BCCA tert-butyl amine salt.isopropanol solvate, BCCA hemi tert-butyl amine salt.hemi ethanol solvate and BCCA.hydrate in crystalline form are non-hygroscopic when stored at ambient temperature. In addition pharmaceutically acceptable salts, such as the calcium and zinc salts, are essentially non-hygroscopic when stored at ambient temperature.

BCCA as the free acid, salt, solvate or hydrate in crystalline form can be prepared according to the following procedures illustrated generally below in Schemes 1, 2, 3 and 4 more specifically described in the following preparations and Examples. The following abbreviations are used herein: ACN refers to acetonitrile; AcOH refers to acetic acid; (S)-BINAP refers to S-(−)-2,2'-bis(diphenylphosphino)-1,1'-binaphthyl; CBZ-Cl refers to benzyl chloroformate; cpd refers to compound; Bn refers to benzyl; DMF refers to dimethyl formamide; Δ refers to the application of heat; DI water refers to deionized water; eq refers to equivalents; erbumine refers to tert-butyl amine (or tert-butyl ammonium salt), 2,2-dimethylethyl amine or 2-methyl-2-propanamine; IPA refers to isopropyl alcohol; M refers to moles/liter; mol refers to moles; MTBE refers to methyl tert butyl ether; N refers to a normal solution; PPTS refers to pyridinium p-toluensulfonate; TFA refers to trifluoroacetic acid; THF refers to tetrahydrofuran; RT refers to room temperature. Unless noted to the contrary, the compounds illustrated herein are named and numbered using CHEMDRAW ULTRA AUTONOM version 7.0.1 or Symyx® Draw version 3.2.
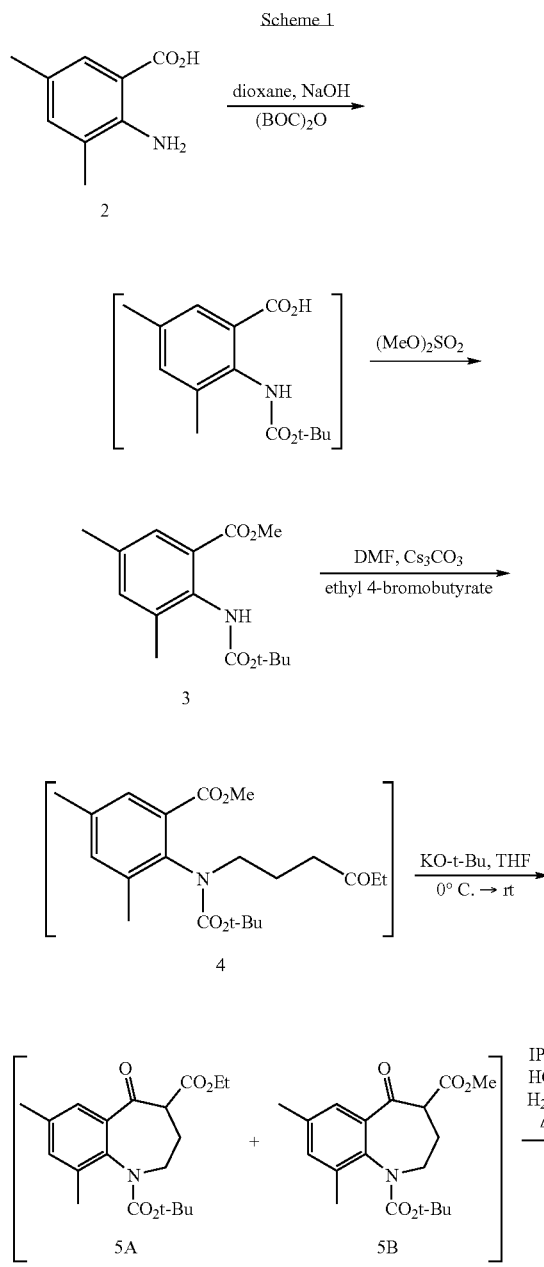
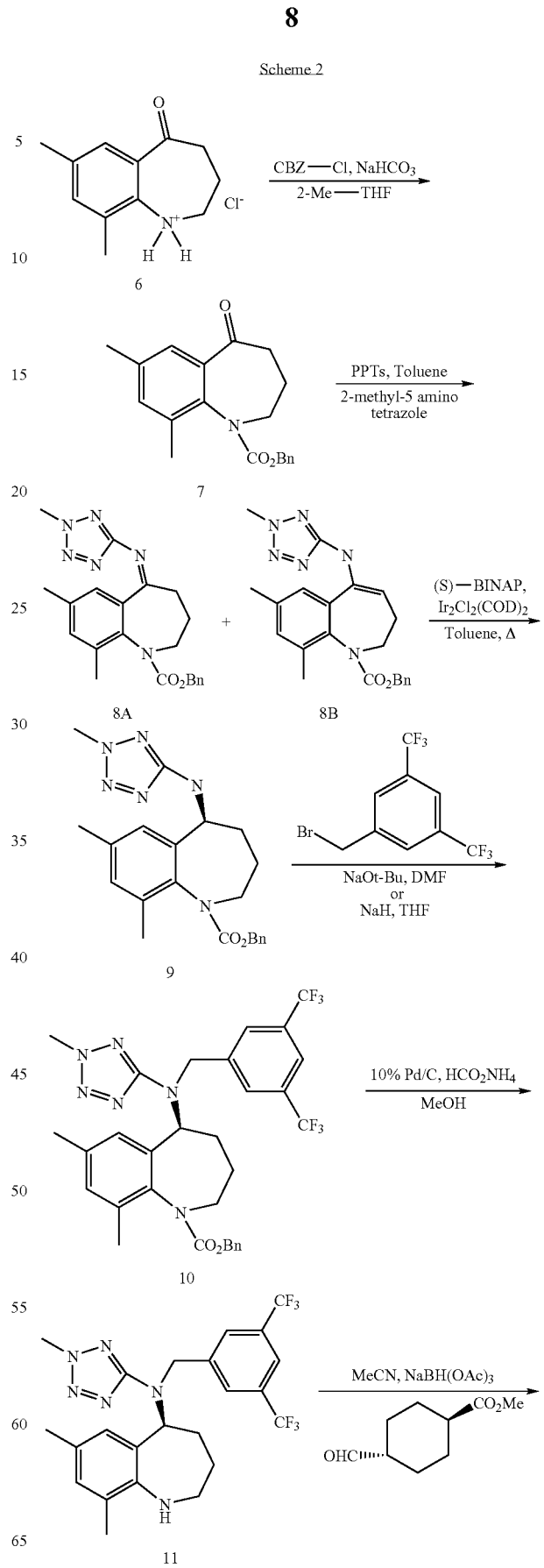

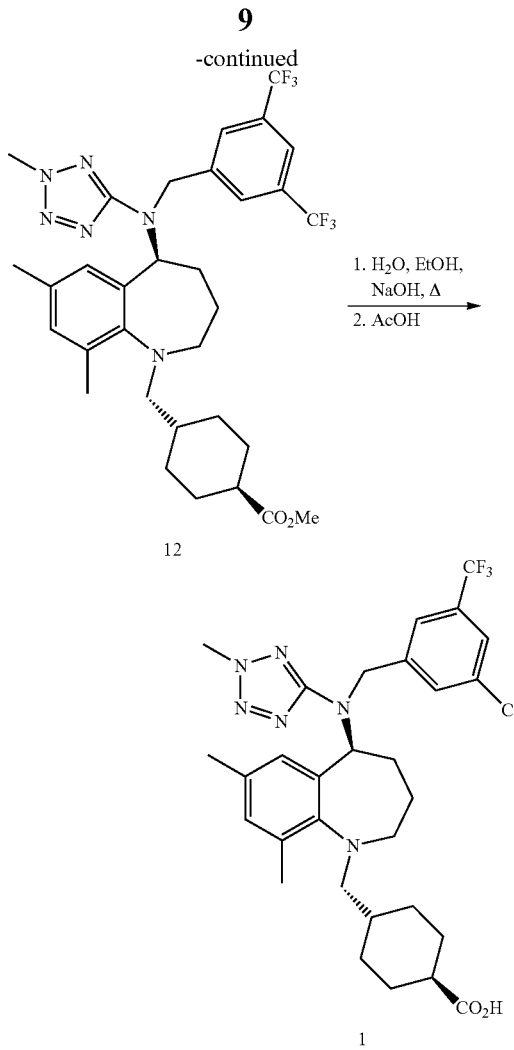

PREPARATIONS

All non-aqueous reactions were performed under a dry atmosphere of nitrogen unless otherwise specified. Unless noted to the contrary, commercial grade reagents and anhydrous solvents were used as received from vendors and no attempts were made to purify or dry these components further. Removal of solvents under reduced pressure was accomplished with a Buchi rotary evaporator at approximately 28 mm Hg pressure using a Teflon-lined KNF vacuum pump. Flash column chromatography was carried out using Kieselgel silica gel 60. Proton NMR spectra were obtained on a Bruker AC 300 MHz Nuclear Magnetic Resonance Spectrometer and are reported in ppm δ values, using tetramethylsilane as an internal reference. The API Mass spectroscopic analyses were performed on a Finnegan LCQ Duo Ion Trap or a PESciex API 150EX mass spectrometer, using electro spray ionization (ESI) or atmospheric pressure chemical ionization (APCI). HPLC analyses were conducted using a Waters Symmetry C18, Sum, WAT046980, 3.9×150 mm column. The elution system consisted of 95:5 (0.1% TFA in $H_2O$)/(0.1% TFA in $CH_3CN$) gradient elution to 0:100 (0.1% TFA in $H_2O$)/(0.1% TFA in $CH_3CN$) over 10 min, followed by 0.1% TFA in $CH_3CN$ isocratic elution for 15 min. The flow rate was 1 mL/min. UV Detection was performed at 254 nm or 220 nm. Selected physical properties as listed above of the preparations and examples were compared to known samples for identification and purity assessment.

Preparation 1

Methyl 2-(tert-butoxycarbonylamino)-3,5-dimethylbenzoate (3)

Charge a 22 L flask, equipped with overhead agitation, condenser, heating mantel, a 5 L addition funnel and $N_2$ purge with 2-amino-3,5-dimethylbenzoic acid (2) (705 g, 4.27 moles, 1.0 eq, prepared essentially according to the procedures disclosed in Chemische Berichte 1992, 125(4), 849-855) and sodium hydroxide (8.08 kg, 8.46 moles). Heat the resulting dark solution to 45° C. with stirring. Charge the addition funnel with di-t-butyldicarbonate (1.92 kg, 9.08 mols) dissolved in 1,4 dioxane (2.75 L, 22.7 moles). Add the di-t-butyldicarbonate solution to the flask and stir over night while maintaining the reaction temperature at about 45° C. Charge the addition funnel with additional di-t-butyldicarbonate (0.961 kg, 4.27 moles), dissolved in 1,4 dioxane 500 mL), and slowly add the contents to the flask while stirring and maintaining the reaction temperature at about 45° C. After the reaction is complete drop wise add dimethyl sulfate (607.1 mL, 6.40 moles); stir overnight while allowing reaction temperature to cool to room temperature. Filter the resulting slurry, collect the solid, and wash with water (2×2 L). Dry in a vacuum (50° C.) to yield the title compound as a crude material (748 g).

Preparation 2

Methyl 2-(tert-butoxycarbonyl(4-ethoxy-4-oxobutyl)amino)-3,5-dimethylbenzoate (4)

Charge a 22 L flask, equipped with overhead agitation, heating mantle, condenser and a $N_2$ purge, with DMF (10 L), ethyl-4-bromobutyrate (1.07 kg, 787.8 mL, 5.32 moles), cesium carbonate (2.92 kg, 22.5 moles), and methyl 2-(tert-butoxy carbonylamino)-3,5-dimethylbenzoate (1,000.0 g, 3.54 moles). Heat the resulting mixture to about 55° C. and stir for about 48 hours. Cool; filter off the solid; and wash the solid with MTBE (2×4 L). Combine the filtrate and the MTBE washings into a 50 L flask and cool to less than about 5° C. Add water (6 L) to quench the reaction. Separate the layers. Wash the aqueous layer with MTBE (3 L); combine the organic layers; and wash the resulting organic solution with brine (2×3 L). Dry the organic solution over $Na_2SO_4$; filter; and wash the collected solids with MTBE to yield 1.582 kg of the title compound.

Preparation 3

Tert-butyl 4-ethyl 7,9-dimethyl-5-oxo-2,3,4,5-tetrahydro-1H-benzo[b]azepine-1,4-dicarboxylate (5A) and tert-butyl 4-methyl 7,9-dimethyl-5-oxo-2,3,4,5-tetrahydro-1H-benzo[b]azepine-1,4-dicarboxylate (5B)

Charge a 22 L flask, equipped with an overhead stirrer, a thermocouple, a 5 L addition funnel, nitrogen purge and a cooling bath, with methyl 2-(tert-butoxycarbonyl(4-ethoxy-4-oxobutyl)amino)-3,5-dimethylbenzoate (700 g, 1.78 moles) dissolved in THF (3.5 L) and cool to less than about 5° C. Charge the addition funnel with 1 M potassium tert-butoxide in THF (KOt-Bu, 3.56 moles, 1M) and dropwise add to the cooled THF solution while maintaining the reaction temperature to a temperature around 5° C. After the addition, if complete, allow the reaction mixture to warm to ambient temperature.

After the reaction is complete, cool the mixture to less than 10° C. and slowly add 2.5 M HCl to provide a mixture with a pH of less than about 3. Add MTBE (4 L) and stir; then separate the organic layer from the aqueous layer. Extract the aqueous layer with MTBE (2 L). Combine the organic layers and sequentially wash with and brine (2×3 L). Dry the organic layer over MgSO$_4$; filter; and rinse the collected solid with MTBE. Combine the filtrate solutions, and remove the solvent under vacuum to yield a mixture of the title compounds as an orange oil (670 g).

Preparation 4

7,9-Dimethyl-3,4-dihydro-1H-benzo[b]azepin-5 (2H)-one hydrochloride (6)

Charge a 5 L flask equipped, with an overhead stirrer, heating mantle, thermocouple, nitrogen purge and a teflon transfer line, with the mixture of tert-butyl 4-ethyl 7,9-dimethyl-5-oxo-2,3,4,5-tetrahydro-1H-benzo[b]azepine-1,4-dicarboxylate and tert-butyl 4-methyl 7,9-dimethyl-5-oxo-2,3,4,5-tetrahydro-1H-benzo[b]azepine-1,4-dicarboxylate (1286 g, 3.56 moles) dissolved in IPA (2 L) and heat the resulting mixture to 50° C. In a separate 12 L flask, equipped with an overhead stirrer, heating mantle, thermocouple, and nitrogen purge to a scrubber, add 5 N NaOH (1 L) and H$_2$O (3 L). Thereafter add HCl (conc, 1.87 L, 21.8 moles) to the 12 L flask and heat to 50° C. Transfer the contents of the 5 L flask to the 12 L flask via the transfer line while flushing with N$_2$ to remove the off gases from the reaction. After the addition, warm the resulting mixture to 80° C., and continue the N$_2$ flush. After the reaction is complete allow the reaction mixture to cool to less than about 20° C. Add MTBE (4 L), and adjust the pH to neutral with aqueous NaOH. Transfer the resulting reaction mixture to a 22 L flask and separate the layers. Wash the aqueous layer with MTBE (2×2 L). Combine the organic washings and wash with brine (2 L), dry over MgSO$_4$, filter and rinse with MTBE. Concentrate the filtrate to a dark oil. Dissolve in IPA (8 volumes) and transfer to a 12 L flask equipped with an overhead stirrer, thermocouple, 1 L addition funnel and N$_2$ purge. Charge the addition funnel with HCl (conc. 765 mL) and add drop-wise over about 1 hr to the IPA solution. Stir the resulting slurry for about 1-2 hrs, filter, rinse the solids with cold IPA (3×500 mL), and dry the solid over night at about 50° C. to yield 561 g of the title compound.

Preparation 5

Benzyl 7,9-dimethyl-5-oxo-2,3,4,5-tetrahydro-1H-benzo[b]azepine-1-carboxylate (7)

Charge a 22 L flask with an overhead stirrer, thermocouple, 3 L addition funnel, baffle, cooling bath and N$_2$ purge and 7,9-dimethyl-3,4-dihydro-1H-benzo[b]azepin-5(2H)-one hydrochloride (1,000 g, 4.43 moles). Add 2-methyltetrahydrofuran (6.44 kg, 7.5 L, 74.5 moles) and agitate the off-white slurry. Cool to 5-15° C. Add water 2.5 L, 138.8 moles and Na$_2$CO$_3$ (1.12 kg, 3 moles) to the addition funnel then slowly add to the reaction mixture at a fast drip over about 25 m. Charge a 2 L addition funnel with benzyl chloroformate (91.59 kg, 8.86 moles) add dropwise to the reaction, while maintaining the reaction mixture below about 15° C. Transfer the resulting mixture to a flask equipped with a condenser and heat to 25-25° C. and stir for about 50 h. Cool to about 15° C., add HCl (5 M, until the pH is about 5). Separate the layers. Extract the aqueous layer with methyltetrahydrofuran (4 L); combine the organic layers and wash with water (4 l). Concentrate the organic layer at about 40° C. Add IPA (4 L) and then concentrate to 2 L. Transfer to a 12 L flask equipped with an overhead stirrer, thermocouple, heating mantle condenser, 2 L addition funnel and N$_2$ purge. Heat the flask contents to about 70-80° C. and add heptane (5 L). Slowly cool to RT overnight; seed the mixture if necessary to induce crystallization of the titled compound. Cool and collect the solid; rinse the solid with cold heptane and dry in a vacuum at 50° C. to provide 1,316 g of the title compound.

Preparation 6

Mixture of (Z)-benzyl 7,9-dimethyl-5-(2-methyl-2H-tetrazol-5-ylimino)-2,3,4,5-tetrahydro-1H-benzo[b]azepine-1-carboxylate (8A) and (E)-benzyl 7,9-dimethyl-5-(2-methyl-2H-tetrazol-5-ylamino)-2,3-dihydro-1H-benzo[b]azepine-1-carboxylate (8B)

Charge a 12 L flask equipped, with an overhead stirrer, heating mantle, thermocouple, condenser, Dean Stark trap, and N$_2$ purge, with benzyl 7,9-dimethyl-5-oxo-2,3,4,5-tetrahydro-1H-benzo[b]azepine-1-carboxylate (920 g, 2.84 moles) and toluene (400 mL). Add toluene (500 mL) to the Dean Stark trap and begin agitation. Add 2-methyl-5-aminotetrazole (563.8 g, 5.69 moles) and PPTS 364.8 g, 0.5 moles) and heat the resulting mixture to reflux. Add cold water 5 L and pour into a NaHCO$_4$ (850 g) solution while monitoring the pH to prevent the mixture from becoming acidic. Separate the layers and wash the aqueous layer with toluene (4 L). Combine the organic layers and wash with water (2×4 L), dry over NaSO$_4$, filter and rinse the solid with toluene. Concentrate the filtrate in vacuo at about 55° C. to yield 1.186 kg of a mixture of compounds title above.

Preparation 7

(S)-benzyl 7,9-dimethyl-5-(2-methyl-2H-tetrazol-5-ylamino)-2,3,4,5-tetrahydro-1H-benzo[b]azepine-1-carboxylate (9)

Charge an autoclave with a mixture of (Z)-benzyl 7,9-dimethyl-5-(2-methyl-2H-tetrazol-5-ylimino)-2,3,4,5-tetrahydro-1H-benzo[b]azepine-1-carboxylate and (E)-benzyl 7,9-dimethyl-5-(2-methyl-2H-tetrazol-5-ylamino)-2,3-dihydro-1H-benzo[b]azepine-1-carboxylate (4.04 g, 10 mmole), S-(−)-2,2'-bis(diphenylphosphino)-1,1'-binaphthyl ((S)-BINAP, 60 mg, 96.3 µmoles), KI (415 mg 24 mmoles, KI can be deleted if desired) and di chloro-bis((1,2,5,6 eta)-1,5-cyclooctadiene)diiridium (Ir$_2$Cl$_2$(COD)$_2$ (927 mg 40.2 µmoles). Purge the autoclave with nitrogen. While maintaining an oxygen free environment, add degassed toluene (50 mL, 472.8 mmol) and seal the autoclave. Heat to 100° C. under 500 psi H$_2$ for 66 h. Cool the reaction mixture to RT and vent. Filter the solids and collect the organic mixture. Wash the organic mixture with water (2×25 mL); dry over Na$_2$SO$_4$, and filter. Collect the filtrate and remove the solvent under vacuum to provide the title compound (3.99 g, 88.7% ee by HPLC).

Preparation 8

(S)-benzyl 5-((3,5-bis(trifluoromethyl)benzyl)(2-methyl-2H-tetrazol-5-yl)amino)-7,9-dimethyl-2,3,4,5-tetrahydro-1H-benzo[b]azepine-1-carboxylate (10)

Charge a vial with (S)-benzyl 7,9-dimethyl-5-(2-methyl-2H-tetrazol-5-ylamino)-2,3,4,5-tetrahydro-1H-benzo[b]

azepine-1-carboxylate (100 mg 246 µmoles), NaH (23 mg 60% in mineral oil, 575.1 µmoles) and THF (9.2 ml, 24.6 mmoles). (Alternatively, potassium tert-butoxide in DMF can be used in place of NaH and THF.) Stir the reaction mixture at RT for 10 m. Add 3,5 bis(trifluoromethyl)benzylbromide (173.8 mg 566.2 µmoles) dropwise over 30 min. After about 19 h, add NaH (10 mg, 60% mineral oil) and stir for an additional 1 h. Partition the reaction mixture between EtOAc (50 mL) and brine (2×25 mL). Collect the organic layers and dry over Na₂SO₄. Filter and then concentrate the filtrate to yield an oil. Partition the oil between ACN (50 mL) and heptane (2×25 mL). Collect the CAN layer; dry to yield an oil (189 mg) of the title compound.

Preparation 9

(S)—N-(3,5-bis(trifluoromethyl)benzyl)-7,9-dimethyl-N-(2-methyl-2H-tetrazol-5-yl)-2,3,4,5-tetrahydro-1H-benzo[b]azepin-5-amine (11)

Charge a 1 L flask with ammonium formate salt (39.0 g, 618.0 mmoles) and 10% Pd/C (3.91 g) and (S)-benzyl 5-((3,5-bis(trifluoromethyl)benzyl)(2-methyl-2H-tetrazol-5-yl) amino)-7,9-dimethyl-2,3,4,5-tetrahydro-1H-benzo[b] azepine-1-carboxylate (39.1 g, 61.8 mmoles) dissolved in MeOH (391 mL, 966 moles). Stir the resulting slurry at RT and monitor by HPLC. After the reaction is complete, filter to collect the solid. Rinse the solid with MeOH (100 mL). Combine the filtrate solutions and organic washes and then dry over Na₂SO₄. Filter and concentrate to dryness. Dissolve in MeOH (92 mL) and seed with seed crystals of the titled compound. Cool and store over night to yield 14.03 g, 45.5% of the titled compound, 99.92% ee by HPLC.

Preparation 10

(Trans)-methyl 4-(((S)-5-((3,5-bis(trifluoromethyl) benzyl)(2-methyl-2H-tetrazol-5-yl)amino)-7,9-dimethyl-2,3,4,5-tetrahydro-1H-benzo[b]azepin-1-yl) methyl)cyclohexanecarboxylate (12)

Charge a flask equipped with an overhead stirrer, temperature probe, nitrogen inlet with (S)—N-(3,5-bis(trifluoromethyl)benzyl)-7,9-dimethyl-N-(2-methyl-2H-tetrazol-5-yl)-2,3,4,5-tetrahydro-1H-benzo[b]azepin-5-amine (5 g, 10.03 mmoles) and sodium triacetoxyborohydride (3.19 g, 15.05 mmoles) and acetonitrile (40 mL) Immerse the flask in an ice bath to cool the slurry to below about 5° C., then add (trans)-methyl 4-formylcyclohexanecarboxylate (2.99 g, 17.57 mmoles, prepared essentially according to the procedures in Houpis, I. N. et al, Tetrahedron Let. 1993, 34(16), 2593-2596 and JP490-48639) dissolved in THF (10 mL) via a syringe while maintaining the reaction mixture at or below about 5° C. Allow the reaction to warm to RT and stir overnight. Add NH₄Cl (25 mL, 50% saturated aqueous solution) and separate the aqueous layer from the organic layer. The pH of the organic layer should be about 5.5. Warm the organic layer to about 45° C. and add water (16 mL). Add a seed crystal of the titled compound and cool to about 35° C. Collect the resulting solid by filtration and rinse with ACN. Dry to provide 5.80 g of the title compound.

Scheme 3: Alternate method for preparing BCCA

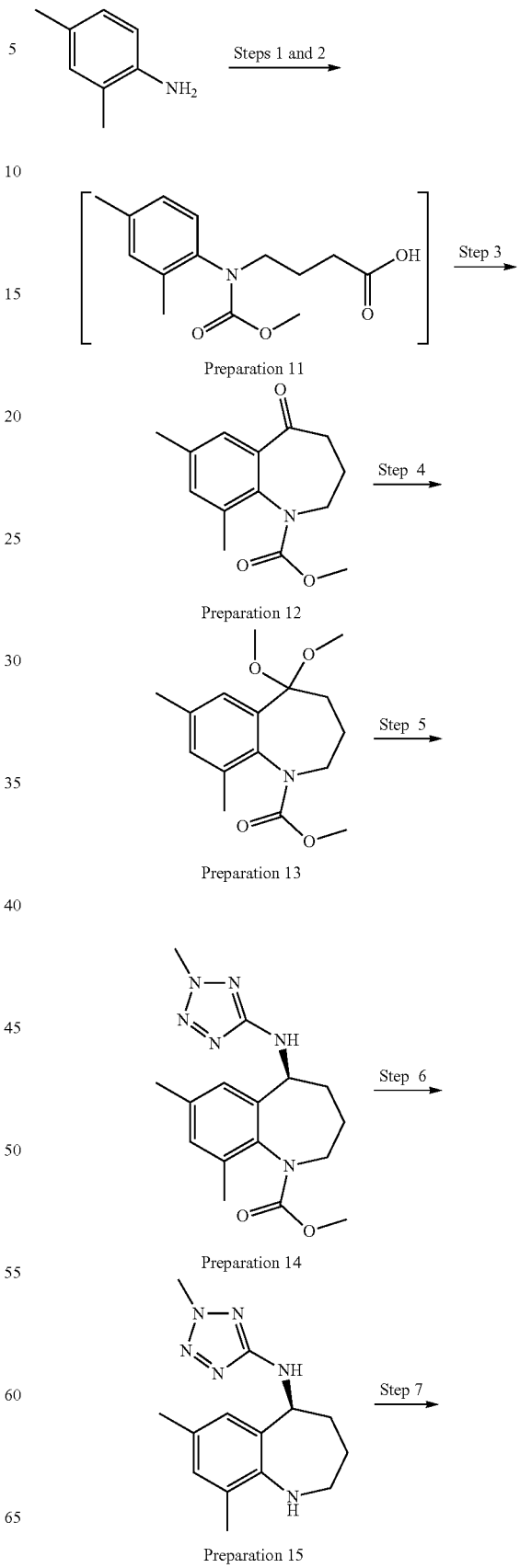

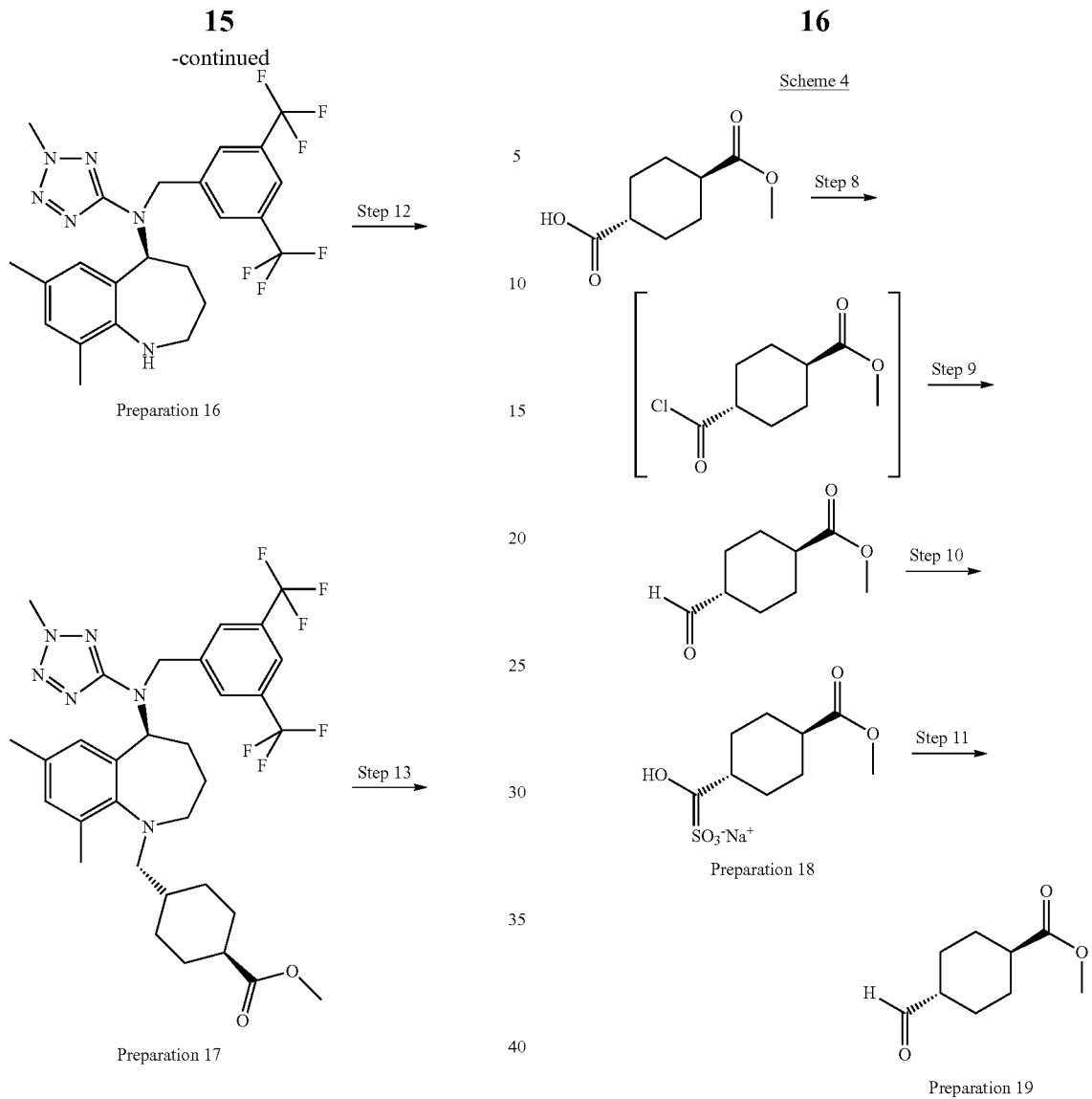

Preparation 12

Methyl 7,9-dimethyl-5-oxo-2,3,4,5-tetrahydro-1H-1-benzazepine-1-carboxylate

Step 1: Evacuate to less than −0.08 MPa a 3000 L glass-lined reactor and then fill with $N_2$ to normal pressure and repeat three times. Under $N_2$, charge the reactor with 2,4-dimethyl aniline (300.0 kg) and triethylamine (873.0 kg) while stirring. Warm the mixture to 70-75° C. and then add ethyl 4-bromobutyrate (604.0 kg) at a rate of 20-25 kg/hour through a 500 L additional vessel while maintaining the 70-75° C. temperature. Stir the mixture at 70-75° C. for 2 hours and then test for reaction completion by GC. The reaction is considered complete when the content of 2,4-dimethyl aniline of two continuous samples is less than 3% and the content of the impurity (ethyl 4-((2,4-dimethylphenyl)(3-(proprionyloxy)propyl)amino)butanoate) is less than 10%. Fifty-six hours later, the content of the impurity is less than 10%, but the content of 2,4-dimethyl aniline is still greater than 3%, so extra ethyl 4-bromobutyrate (6.0 kg) is added to the mixture, then 17.5 hours later, the content of 2,4-dimethyl aniline is still greater than 3% but the reaction is quenched.

Cool the reaction to 15-25° C. and transfer to two 5000 L glass-lined reactors. For each reactor, add water (1200.0 kg) and toluene (1044.0 kg). Stir the mixture for one hour and hold for one hour before separation. Combine the organic phase of the two reactors and wash with water (1200.0 kg×2) twice. Sample the organic phase to ensure the triethylamine is less than 23%.

Concentrate the organic phase at 50-60° C. under reduced pressure (≦−0.08 MPa) until no fraction came out and the weight % of triethylamine is less than 0.1% and the KF is less than 1%. Cool the mixture to 20-30° C. and use the product (ethyl 4[(2,4 dimethylphenyl)amino]butanoate) in the Step 2 directly.

Gas chromatograph (GC): column. HP-5, 30 m length× 0.32 mm ID×0.25 μm film or column equivalent; carrier gas: Helium gas; flow rate 1.90 mL/min; run time: 22.5 min; Program: Initial temp: 50° C. (On) and Initial time: 2.00 min; Ramps: 1 Rate: 20 Final temp: 260 Final time: 10.00; Ramp #2: 0.0 (Off); inlet temp 250° C.; detection temp: 300° C.

Ret times: 1) (13.56 min) ethyl 4[(2,4 dimethylphenyl) amino]butanoate; 2) (17.40) ethyl 4-((2,4-dimethylphenyl) (3-(proprionyloxy)propyl)amino)butanoate; 3) (8.38 min) 2,4-dimethyl aniline.

Step 2: Charge a 2000 L glass-lined reactor with toluene (742.0 kg) and ethyl 4[(2,4 dimethylphenyl)amino]butanoate (171.0 kg). Stir the mixture and add sodium carbonate (77.0 kg) in portions. Maintain the temperature at 20-25° C. and add methyl chloroformate (96.2 kg) at a rate of 18 kg/hour. Stir the mixture at 20-25° C. and monitor after one hour by GC. The reaction is considered complete when content of ethyl 4[(2,4 dimethylphenyl)amino]butanoate is less than 1%. Transfer the mixture to a 5000 L glass-lined reactor and rinse the 2000 L with toluene (75 kg). Add a solution of NaOH (87.2 kg), methanol (934.0 kg) and water (1482.0 kg) at a rate of 360-400 kg/hour while maintaining the temperature at 20-25° C. Then, heat the mixture to 55-65° C. and stir at 55-60° C. After one hour, test a sample by HPLC to determine the level of ethyl 4[(2,4 dimethylphenyl)amino]butanoate. Cool the mixture to 20-30° C., hold for one hour, and then separate. Concentrate the aqueous phase at 40-50° C. under reduced pressure (less than or equal to 0.09 MPa) until 929 kg of methanol distilled out.

Cool the mixture to 15-25° C., add water (256.5 kg), stir for 0.5 hr, and extract with dichloromethane (342.0 kg×2). Reduce the temperature to 0-5° C. and maintain, and add conc. HCl (269.0 kg) at the rate of 40-50 kg/hour to adjust the pH to 1-2. Heat the mixture to 15-25° C. and stir for 1 hour while maintaining this temperature. Separate, extract the aqueous phase with dichloromethane (684.0 kg×2), and combine the organic phases. Wash the organic phase twice with 0.5% HCl (342.0 kg×2) and then twice with conc. HCl (3.4×2 kg). Concentrate the organic phase under reduced pressure (less than or equal to −0.08 MPa; 40-50° C.) until no fraction came out. Add dichloromethane (250.0 kg) to the residue (4-[(2,4-dimethylphenyl)-methoxycarbonyl-amino]butanoic acid) (Preparation 11) and use in the next step directly. 190.0 kg (407.4 kg solution); Yield: 98.5%; Purity: 97.8%.

HPLC: column. Waters XTerra MS C18; 4.6×150 mm, 3.5 μm; 230 nm detection; flow rate of 1.0 ml/min; temp 25° C.; isocratic mobile phase: A:ACN; B:$H_2O$+0.1% $H_3PO_4$ (v/v). Ret time: (13.86 min) 4-[(2,4-dimethylphenyl)-methoxycarbonyl-amino]butanoic acid.

Step 3: Evacuate a 3000 L glass-lined reactor to less than −0.08 MPa, fill with nitrogen gas to normal pressure, and repeat for 3 times. Charge with dichloromethane (1900.0 kg), 4-[(2,4-dimethylphenyl)-methoxycarbonyl-amino]butanoic acid (190.0 kg) and DMF (11.4 kg) and stir. Cool the mixture to −5-0° C., and while maintaining this temperature, add thionyl chloride (85.3 kg) at the rate of 18 kg/hr. Stir the mixture at −5-0° C. One later, monitor the reaction by HPLC to determine if the content of 4-[(2,4-dimethylphenyl)-methoxycarbonyl-amino]butanoic acid is less than 1%. For sampling, add the sample to methanol and evaluate by HPLC. Concentrate the mixture at 40-45° C. under normal pressure until no more fraction is observed, and then cool to 15-25° C. Then, concentrate at 40-45° C. under reduced pressure (less than or equal to −0.08 MPa) until no more fraction is observed. Dilute with dichloromethane (1031.0 kg). Add drop wise a solution of dichloromethane (1030.0 kg) and anhydrous aluminum chloride hexahydrate (287.2 kg) at 30-35° C. Stir the mixture at 35-45° C. for 2 hrs later and then monitor by HPLC until the content of Methyl 7,9-dimethyl-5-oxo-2,3,4,5-tetrahydro-1H-1-benzazepine-1-carboxylate is greater than 80%. (Take the mixture, add it into methanol and send it to be detected by HPLC) Quench the mixture with a mixture of water (1140.0 kg) and ice (570.0 kg) and maintain the temperature at 0-10° C. and stir for 1 hour. Warm the mixture to 15-25° C., stir for 0.5 hr, hold for 0.5 hr and separate. Wash the organic phase with water (814.0 kg×2). Add silica gel (380.0 kg) to the organic phase and stir the mixture for 1 hour. Filter the mixture, rinse the cake with dichloromethane (339.0 kg) and combine the filtrate. Concentrate the filtrate at 40-45° C. under reduced pressure (less than or equal to −0.08 MPa) until 150-200 L mixture remains.

Add heptane (190.0 kg), cool the mixture to 15-20° C. by recycle water, and then cool to 0-5° C. by brine. Stir the mixture at this temperature to crystallize. Filter the mixture, dry the filter cake at 35-40° C. in a drying room to obtain 80.9 kg of off-white solid. HPLC 97.9%. Store in a dry and sealed place under the protection of nitrogen.

HPLC procedure: same as for step 2 above. Ret time (14.71 min) methyl 7,9-dimethyl-5-oxo-2,3,4,5-tetrahydro-1H-1-benzazepine-1-carboxylate.

Preparation 13

Methyl 5,5-dimethoxy-7,9-dimethyl-2,3,4,5-tetrahydro-1H-1-benzazaepine-1-carboxylate Step 4: To a solution of methyl 7,9-dimethyl-5-oxo-2,3,4, 5-tetrahydro-1H-1-benzazepine-1-carboxylate (1000 g; 1.00 equiv; 4.04 moles) in methanol (2.50 L) and trimethoxymethane (9.10 moles; 995.42 mL; 965.55 g) equipped with an overhead stirrer at ambient temperature under a blanket of nitrogen, add Amberlyst™ 15 (100 g). Heat the reaction mixture to 50° C. and maintain the temperature for 1 hour. After 1 hour, the reaction is complete.

Cool the reaction mixture to ambient temperature and filter the Amberlyst beads and rinse with methanol (500 mL). Set up a cannula and add the solution into a 0.1 M KOH solution (1 L) with overhead stirring, followed by $H_2O$ (1500 mL). Stir the slurry for 20 min and then filter using a 32 cm ceramic filter with a polypropylene pad. Wash the cake with 4×1 L of water and pull to dryness on the filter. Dry in the vacuum oven overnight at 60° C. After overnight, break the chunks up and continue to dry at 60° C. overnight. Crude yield after drying: 1235 g. Dissolve crude solids in 5 volumes of heptane (6 L), heat to 70° C., and stir 15 min at 70° C. Cool the solution to 55° C., at which point the reaction is seeded. Continue to cool slowly and the product starts to come out at ~45° C. Continue to cool slowly to room temperature and then let the slurry stir overnight. Filter the product slurry over a polypropylene pad. Rinse the cake with 2×500 mL of heptane. Pull dry on the filter and then place in the vacuum oven at 45° C. until dry (~4 days). 766 g. 99.9% pure by HPLC.

HPLC: Zorbax Bonus-RP 50×4.6 mm, 1.8 μm; 2 ml/min, 40° C., 10-30% ACN over 12 min, to 95% at 14 min, hold 2 min, re-equilibrate balance of eluent is 10 mM NH$_4$acetate. Ret time=13.77 min.

Preparation 14

Methyl-(5S)-7,9-dimethyl-5-[(2-methyl-2H-tetrazol-5-yl)amino]-2,3,4,5-tetrahydro-1H-1-benzazepine-1-carboxylate Step 5: Ensure hydrogen reactor is dry by drying with N$_2$ for 1-2 hours. Add 2-methyl-2H-tetrazol-5-amine (52.0 g), methyl 5,5-dimethoxy-7,9-dimethyl-2,3,4,5-tetrahydro-1H-1-benzazaepine-1-carboxylate (140.0 g), Ir$_2$Cl$_2$(COD)$_2$ (0.080 g), TBAI (1.76 g), (1S)-(+)-10-camphorsulfonic acid (2.2 g), and (S)-difluorphos (0.163 g) to the reactor. Put 5 psi nitrogen on the reactor. Add 600 mL toluene (sparged with N$_2$ for 75 min.) via cannula/nitrogen. Purge the reactor 2 times with 20 psi nitrogen and do not allow pressure to go below 5 psi. Place 500 psi of hydrogen on the reactor and warm slowly to 115° C. Hold at this temperature overnight. Cool to 50° C. and sample for HPLC analysis. For chiral HPLC, dilute sample with toluene, wash with sodium bicarbonate, dry on Na$_2$SO$_4$, dilute with heptanes/ethanol.

Pour the toluene solution into a separatory funnel and add 140 mL of ethyl acetate to get everything into the separatory funnel and to keep everything in solution during the work-up. Wash the solution with 420 mL of 1 M NaOH solution (the organic layer looks cloudy; aqueous layer clear). Separate the layers and wash the organic layer with 420 mL of H$_2$O. Distill the organic layer at atmospheric pressure to 1.5 volumes of toluene (2.5 volumes total solution remaining). Cool the solution to 60° C. and add 700 mL of heptane (~5V) slowly over 3 min at 60° C. and heat the resulting clear solution at 60° C. overnight with overhead stirring (150 rpm). After 15 min, there is more solid. In the morning, cool the slurry, filter, collect the solid material and dry in a vacuum oven at 60° C. for 3 hours. 126.97 g, HPLC: 99.4% pure, Chiral HPLC: 94.6% ee.

HPLC: Zorbax Bonus-RP 50×4.6 mm, 1.8 μm; 2 ml/min, 40° C., 10-30% ACN over 12 min, to 95% at 14 min, hold 2 min, re-equilibrate balance of eluent is 10 mM NH$_4$acetate. Ret time=11.36 min.

Chiral HPLC: Chiralpak IA 250×4.6 mm, 2 ml/min, 40° C., 5% IPA for 11 min, to 50% IPA at 12 min, hold to 15 min, back to 5% IPA at 15.1 min, hold for 20 min. Ret time=11.48 min.

Preparation 15

(5S)-7,9-dimethyl-N-(2-methyltetrazol-5-yl)-2,3,4,5-tetrahydro-1H-1-benzazepin-5-amine Step 6: Combine methyl-(5S)-7,9-dimethyl-5-[(2-methyl-2H-tetrazol-5-yl)amino]-2,3,4,5-tetrahydro-1H-1-benzazepine-1-carboxylate (20.1 g), NaOH (12.10 g), and ethanol (80 mL) in a 250 mL teflon flask with overhead stirring. Sparge with nitrogen for 10 minutes, heat to reflux (85° C.) for ~5.5 hours. Cool to room temperature with a cool water bath. Add acetic acid/water (17.5 mL/53 mL) slowly at room temperature and transfer to 500 mL flask about half way through addition (~30 min total time for addition). Seed with ~5 mg of (5S)-7,9-dimethyl-N-(2-methyltetrazol-5-yl)-2,3,4,5-tetrahydro-1H-1-benzazepin-5-amine Heat to 50° C. (up to temperature in about 15 minutes). Add 54 mL of water over about 30 minutes. The next day, cool in ice bath, filter and rinse with methanol:water (1:1; 2×30 mL). Dry wet cake in vacuo at 60° C. to yield 13.99 g of (5S)-7,9-dimethyl-N-(2-methyltetrazol-5-yl)-2,3,4,5-tetrahydro-1H-1-benzazepin-5-amine HPLC analysis: 99.4%, ret time is 4.84 min. Chiral HPLC: 98.5% chiral purity.

HPLC method: Zorbax SB-C8 75×4.6 mm, 3.5 μm, 2 mL/min, 40° C., 225 nm wavelength, 5% acetonitrile (ACN) for 2 min to 95% ACN in 10 min and hold for 1 min.

Chiral HPLC: Chiralpak AD-H 150×4.6 mm, 5 μm, 1 ml/min, 30° C., isocratic 50% ethanol in heptane.

Preparation 16

(5S)—N-[3,5-bis(trifluoromethyl)benzyl]-7,9-dimethyl-N-(2-methyl-2H-tetrazol-5-yl)-2,3,4,5-tetrahydro-1H-1-benzazepin-5-amine Step 7: Degas all liquids prior to addition to the reaction by saturating each solution by subsurface addition of N$_2$. To a 250 mL flask with a nitrogen inlet, add (5S)-7,9-dimethyl-N-(2-methyltetrazol-5-yl)-2,3,4,5-tetrahydro-1H-1-benzazepin-5-amine (18.36 mmoles; 5.00 g) and toluene (15.00 mL). Add drop wise over 30 minutes potassium hexamethyldisilazide (19.28 mmoles; 38.55 mL) as a 0.5M solution in toluene. An exotherm is observed to 21.5° C. Stir the reaction mixture for 30 minutes. Add over 30 minutes 1-(chloromethyl)-3,5-bis(trifluoromethyl)benzene (25.71 mmoles; 25.7 mL) as a 1 M solution in toluene. An exotherm is observed to 25.5° C. Stir the reaction mixture at room temperature for 16 hours. Wash the reaction mixture with water (2×20 mL). Combine the water layers and back extract with toluene (1×25 mL). Combine the toluene layers, concentrate to dryness, and recrystallize the residue from 92 mL of 60% 1-propanol in water. Stir the crystallized product for 2 hours at 0° C., filter, and rinse with 10 mL of 50% 1-propanol in water. Dry the isolated product in vacuum at 45° C. 7.735 grams. HPLC shows 98.3% pure, ret time=10.62 min.

Gradient HPLC: Column is Zorbax Bonus RP 5 μm, 4.6×150 cm, Flow=2 mL/min; Wavelength=225 nm; Column temp=40° C.; Solvent A=Water; Solvent B=ACN; Time 0 min 85% A 15% B; 12 min 10% A 90% B; 13 min 10% A 90% B; 13.5 min 85% A 15% B.

Preparation 17

Methyl-trans-4-{[(5S)-5-{[3,5-bis(trifluoromethyl)benzyl](2-methyl-2H-tetrazol-5-yl)amino}-7,9-dimethyl-2,3,4,5-tetrahydro-1H-1-benzazepin-1-yl]methyl}cyclohexanecarboxylate Step 12: Cool a suspension of (5S)—N-[3,5-bis(trifluoromethyl)benzyl]-7,9-dimethyl-N-(2-methyl-2H-tetrazol-5-yl)-2,3,4,5-tetrahydro-1H-1-benzazepin-5-amine (3.40 g, 6.82 mmol), sodium triacetoxyborohydrate (3.01 g, 13.64 mmol), and ACN (28 mL) to −12° C. to −10° C. in an ice/acetone bath and add a solution of (trans)-4-formylcyclohexanecarboxylate (2.03 g, 11.93 mmol) in toluene (18.5 mL) over 30 min via a syringe pump (0.66 mL/min). Continue stirring the reaction in an ice/acetone bath for 2 hours. Add 44 mL of 10% (by weight) NH4Cl in water to the reaction and stir for 30 min at room temperature. Stop stirring and there are two layers. Separate the layers, concentrate the organic layer down to one volume of solvent. Add 24 mL of ethanol and concentrate to a solid (or to one volume). Add 24 mL of ethanol, 2 mL of water and heat to 60° C. (still a suspension). Add 2 mL of water dropwise. Allow the suspension to cool to room temperature and stir overnight at room temperature. After stirring overnight at room temperature, cool the suspension to −10° C. for 0.5 h, then filter. Wash the filter solids with 3 mL of −10° C. EtOH:water (4:1). Dry the solids overnight in a vacuum oven at 50° C. to give 4.24 g of methyl-trans-4-{[(5S)-5-{[3,5-bis(trifluoromethyl)benzyl](2-methyl-2H-tetrazol-5-yl)amino}-7,9-dimethyl-2,3,4,5-tetrahydro-1H-1-benzazepin-1-yl]methyl}cyclohexanecarboxylate as a colorless solid. HPLC shows 99.75% pure.

HPLC analysis: Zorbax Bonus RP 150 mm×4.6 mm, 3.5 μm, 30° C., 260 nm UV detection, flow: 2.0 mL/min, gradient: A=0.05% TFA in H2O, B=0.05% TFA in ACN; 0 min 95% A to 30 min 0% A to 30.5 min 95% A to 35 min 95% A. Methyl-trans-4-{[(5S)-5-{[3,5-bis(trifluoromethyl)benzyl](2-methyl-2H-tetrazol-5-yl)amino}-7,9-dimethyl-2,3,4,5-tetrahydro-1H-1-benzazepin-1-yl]methyl}cyclohexanecarboxylate elutes at 23.33 min and the cis isomer elutes at 23.05 min.

Preparation 18

Sodium bisulfate adduct of (trans)-methyl-4-formylcyclohexanecarboxylate

Step 8: Place a 12 L three-neck round-bottom flask into a cooling tub equipped with a mechanical stirrer, thermocouple with display, nitrogen inlet, and drying tube. Charge (trans)-4-methoxycarbonylcyclohexanecarboxylic acid (450 g) to the flask. Charge dichloromethane (2.25 L) to the flask and stir under nitrogen. Add oxalyl chloride (364 g dissolved in $CH_2Cl_2$ (100 mL)) to the flask via addition funnel at ambient temperature. Stir the reaction mixture for 10 minutes at room temperature. Add catalytic amount of DMF (1.82 g dissolved in $CH_2Cl_2$ (10 mL)) to the flask via addition funnel at ambient temperature. Stir the reaction mixture at a temperature less than 20° C. for 2 hours. Monitor the reaction progress by GC: [DBI 30 m×0.25 mm, 0.5μ), remove a sample of the stirring solution at a temperature less than 20° C. Retention time (Rt) of (trans)-4-chlorocarbonylcyclohexane carboxylate=7.3 minutes; Rt of (trans)-4-methoxycarbonylcyclohexanecarboxylic acid=7.75 minutes. The reaction is deemed complete when <3.0% of the starting material (trans)-4-methoxycarbonylcyclohexane-carboxylic acid remains.

Step 9: Concentrate the reaction mixture under reduced pressure at a temperature less than 35° C. Collect excess oxalyl chloride along with the distillate; use a caustic trap to prevent acidic vapors from entering into the vacuum system. Co-evaporate the residue with THF (2×900 mL). Dilute the residue with THF (4.5 L) and 2,6-lutidine (321 g). Transfer to a hydrogenation auto-clay reactor. Charge the 5% Pd on activated carbon {(45 g slurried in THF (500 mL)) to the reaction mixture. Purge the reactor with nitrogen gas (20 to 30 psi) 2 to 3 times. Purge with hydrogen gas (20 to 30 psi) 2 to 3 times. Stir the reaction under hydrogen atmosphere (50 to 60 psi) for 15 hours at 30 to 35° C. After 15 hours, exit the hydrogen gas to the local exhaust and purge the reactor with nitrogen gas (20 to 30 psi) for 2 to 3 times. Monitor the reaction by GC. Rt of (trans)-methyl-4-formylcyclohexane carboxylate=6.46 minutes; Rt of (trans)-4-chlorocarbonylcyclohexanecarboxylate=7.3 minutes. The reaction is deemed complete when less than 1.0% of (trans)-4-chlorocarbonyl cyclohexanecarboxylate remains.

Filter the reaction mixture through the pad of celite under nitrogen. Concentrate most of the THF solvent under reduced pressure at a temperature less than 35° C. Dilute the residue with MTBE (1.8 L) and transfer to a separatory funnel Wash the organic solution with water (2.25 L) and separate the layers. Back extract the aqueous phase with MTBE (2×1.8 L) and combine the all organic layers. Wash with a 0.5 N aqueous solution of hydrochloric acid (1×2.25 L). Wash the organic phase with a saturated aqueous solution of sodium bicarbonate (1×2.5 L). Wash the organic phase with a brine solution (1×2.5 L). Dry the organic phase over magnesium sulfate and filter the mixture onto a glass-fiber filter pad. Concentrate the filtrate under reduced pressure at a bath temperature of less than 35° C. Isolate the crude material as a colorless oil and use without any further purification.

Step 10: Add 1 mL of water to a vial containing 0.49 g of sodium bisulfite. Place the vial in the sonicator to dissolve the sodium bisulfite. Add 5 mL of THF to the vial (a biphasic solution forms—no solids) Add this biphasic solution of THF and aqueous sodium bisulfite to a 50 mL flask equipped with a magnetic stirrer containing (tr ans)-4-formylcyclohexane carboxylate (1 g, 5.88 mmol). (Note: the (trans)-4-formylcyclohexanecarboxylate is only about 80% pure, so this is why 0.8 equiv of $NaHSO_3$ is used.) Dilute the solution with another 5 mL of THF and within one minute a very thick mass of crystals forms. Heat the mass of crystals to reflux. Dilute the mixture with 3×5 mL of THF. The crystals are very flocculent. Stirred at room temperature for several hours, then filter, rinse with 20 mL THF and dry on the filter for an hour (1.27 g). Dry overnight in a vacuum oven at 40° C. to give 1.19 g of sodium bisulfate adduct of (trans)-methyl-4-formylcyclohexanecarboxylate as a colorless solid.

Preparation 19

(trans)-4-formylcyclohexanecarboxylate

Step 11: Add Sodium bisulfate adduct of (trans)-methyl-4-formylcyclohexanecarboxylate (3.92 g, 11.93 mmol) to a mixture of sodium carbonate (5.06 g, 47.72 mmol), toluene (17 mL) and water (33 mL) and stir at room temperature. After stirring 1 hour at room temperature, separate the layers and wash the toluene layer with 15 mL of water. Use this toluene solution that contains (trans)-4-formylcyclohexanecarboxylate in Step 12.

Example 1

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid Amorphous Solid Charge a flask with (trans)-methyl 4-(((S)-5-((3,5-bis(trifluoromethyl)benzyl)(2-methyl-2H-tetrazol-5-yl)amino)-7,9-dimethyl-2,3,4,5-tetrahydro-1H-benzo[b]azepin-1-yl)methyl)cyclohexanecarboxylate (149 mg). Add MeOH (6 mL) and 1.0 N NaOH (3.0 mL). Heat the resulting mixture to about 60° C. Monitor the reaction via TLC. After about 7 hrs or when the starting ester has reacted, cool the mixture to about 0° C. and quench with 1 N HCl. Dilute the mixture with EtOAc (60 mL). Sequentially wash the mixture with water (20 mL), brine (20 mL) and dry over $Na_2SO_4$. Filter and concentrate the filtrate. Purify via flash chromatography with $CH_2Cl_2$. Remove the solvent to provide the title compound (125 mg) as a white solid.

Example 2

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid Amorphous Solid Charge a 500 mL 3-neck flask equipped with a mechanical stirrer, addition funnel, and thermocouple with water (265 mL) and cool in an ice bath. Dissolve BCCA (22.0 g) in 40 mL acetone in a second flask and add the mixture to the three-neck flask via the addition funnel Rinse the flask with an additional 4 mL of acetone and add to the funnel Dropwise add the contents of the addition funnel to the flask and allow the resulting mixture to stir while maintaining the temperature at about 0-1° C. Collect the resulting solid, wash twice with water then dry at 40° C. overnight to provide 22.3 g of a white powder.

Example 3

Trans-4-[[(5S)-5-[[[3,5-bis(trifluoromethyl)phenyl]
methyl](2-methyl-2H-tetrazol-5-yl)amino]-2,3,4,5-
tetrahydro-7,9-dimethyl-1H-1-benzazepin-1-yl]me-
thyl]-cyclohexanecarboxylic acid.Hydrate Purge a flask equipped with an overhead stirrer, temperature probe, nitrogen inlet with nitrogen then while maintaining a positive nitrogen atmosphere in the flask add (trans)-methyl 4-(((S)-5-((3,5-bis(trifluoromethyl)benzyl)(2-methyl-2H-tetrazol-5-yl)amino)-7,9-dimethyl-2,3,4,5-tetrahydro-1H-benzo[b]azepin-1-yl)methyl) cyclohexanecarboxylate (1.0 kg 1.53 mol), MeOH (10 L), and NaOH 2 M (1.53 L, 3.06 mol.). Heat the resulting mixture to reflux about 68° C. After about 4 hrs allow the reaction mixture to cool to RT and stir overnight. Filter the mixture and collect the filtrate. Add a MeOH:Water mixture (500 ml 1:1 v/v) and then slowly add acetic acid (260 mL) to induce precipitation. Collect the resulting solid as a mixture of BCCA, the BCCA hydrate and the BCCA.methanol solvate. Dry the solid in an oven at 40° C.

Charge a 2 L flask equipped with a condenser, thermocouple, heating mantle and mechanical stirrer with the BCCA solid material (109 gm), MeOH (900 mL) and water (10 mL). Heat the resulting slurry to reflux under a nitrogen atmosphere. After all the solids dissolve, remove the heat and allow the mixture to cool to ambient temperature. If desired a seed crystal of BCCA hydrate in crystalline form can be added. Collect the solid material. Sequentially wash the solid with methanol:water (9:1 v/v, 100 mL) and water (1 L). Dry the solid in a vacuum at about 40° C. to provide 100 g of a white solid. Thereafter reslurry the solid in isopropanol:water (1:1 v/v 1 L). Collect the resulting solid and rinse with water (500 mL) and dry overnight in vacuo at about 40° C. to provide 60 g of the title compound. Analysis Karl Fisher 2.53% water, elemental analysis:

$C_{31}H_{36}F_6N_6O_2H_2O$ theoritical (%) C, 56.70; H, 5.83; N, 12.80. found (%): C, 56.59; H, 5.28; N, 12.55.

Solid State NMR $^{13}C$ Cross polarization/magic angle spinning (CP/MAS) NMR (solid-state NMR or SSNMR) spectra of crystalline BCCA.hydrate in crystalline form, which was obtained using a Bruker Avance II 400 MHz NMR spectrometer operating at a carbon frequency of 100.622 MHz and equipped with a Bruker 4 mm double resonance probe (K299552). TOSS sideband suppression was used along with cross polarization employing SPINAL64 decoupling (95.4 Watts) and a RAMP100 shaped H-nucleus CP pulse. Acquisition parameters were as follows: 90° proton r.f. pulse width of 2.50 µs, contact time was 1.5 ms, pulse repetition time of 20 s, MAS frequency of 5 kHz, spectral width of 30 kHz, acquisition time was 34 ms and the number of scans was 3,844. Representative resononances from the $^{13}C$ SSNMR BCCA.hydrate include: 175.6, 168.0, 145.6, 144.8, 143.5, 139.9, 136.3, 132.8, 132.1, 129.2, 127.3, 126.2, 122.7, 121.0, 61.1, 53.0, 49.8, 45.0, 40.2, 38.7, 31.4, 30.4, 29.0, 27.8, 27.0, 21.2, 18.3, +/−0.2 ppm. Chemical shifts were referenced to adamantane (δ=29.5 ppm) in a separate experiment.

Example 4

Trans-4-[[(5S)-5-[[[3,5-bis(trifluoromethyl)phenyl]
methyl](2-methyl-2H-tetrazol-5-yl)amino]-2,3,4,5-
tetrahydro-7,9-dimethyl-1H-1-benzazepin-1-yl]me-
thyl]-cyclohexanecarboxylic acid Hydrate and
Ethanol Solvate in Crystalline Form Charge a flask with (trans)-methyl 4-(((S)-5-((3,5-bis(trifluoromethyl)benzyl)(2-methyl-2H-tetrazol-5-yl)amino)-7,9-dimethyl-2,3,4,5-tetrahydro-1H-benzo[b]azepin-1-yl)methyl)cyclohexanecarboxylate (12.95 kg) EtOH (129.5 L) and 2 M NaOH (9.9 L, 2 eq) stir the resulting mixture for about 10 min and thereafter heat the reaction mixture to about 40-45° C. for 6 hrs. Monitor the reaction via HPLC. Thereafter add acetic acid (3.75 kg) followed by water (15.5 L) and seed with BCCA.hydrate in crystalline form. After stirring about 2 hrs, cool the reaction mixture to RT and stir for an additional 2 hrs. Collect the resulting solids; wash the solids with EtOH:water (1:1, 2×26 L) and dry over night to yield the title compound 15.87 kg (wet) to as a mixture of the ethanol solvate and the hydrate.

Example 5

Trans-4-[[(5S)-5-[[[3,5-bis(trifluoromethyl)phenyl]
methyl](2-methyl-2H-tetrazol-5-yl)amino]-2,3,4,5-
tetrahydro-7,9-dimethyl-1H-1-benzazepin-1-yl]me-
thyl]-cyclohexanecarboxylic acid hydrate in
crystalline form Charge a flask with Trans-4-[[(5S)-5-[[[3,5-bis(trifluoromethyl)phenyl]methyl](2-methyl-2H-tetrazol-5-yl) amino]-2,3,4,5-tetrahydro-7,9-dimethyl-1H-1-b enzazepin-1-yl]methyl]-cyclohexanecarboxylic acid (15.87 kg) and water (158.8 L). Stir the resulting mixture at RT for 2 hrs. Thereafter filter the resulting mixture to collect the solids. Dry the solids over night. The resulting solids were dissolved in MeOH heated to about 65-70° C. for 2 hrs to provide a clear solution. Filter the clear solution, then cool the filtrate to about 0 to 5° C. to induce crystallization. Collect the resulting crystals, and dry overnight. Suspend the crystalline material in water (158.8 L) and stir for about 2 hrs at RT. Collect the crystalline solid; dry at high vacuum at 40-45° C. to provide a solid that exhibits a water content of between 2.7 to 3.1 as determined by the Karl Fischer method.

Example 6

Crystallization of Trans-4-[[(5S)-5-[[[3,5-bis(trifluoromethyl)phenyl]methyl](2-methyl-2H-tetrazol-5-yl)
amino]-2,3,4,5-tetrahydro-7,9-dimethyl-1H-1-benza-
zepin-1-yl]methyl]-cyclohexanecarboxylic acid
Hydrate Charge a 250 mL flask equipped with an overhead stirrer, with ethanol (100 mL), (trans)-methyl 4-(((S)-5-((3,5-bis(trifluoromethyl)benzyl)(2-methyl-2H-tetrazol-5-yl)amino)-7, 9-dimethyl-2,3,4,5-tetrahydro-1H-benzo[b]azepin-1-yl)methyl)cyclohexanecarboxylate (10.0 g, 15.32 mmoles) and NaOH (2 M, 15.0 mL, 30.0 mmoles). Warm the resulting mixture to about 40° C. and stir at that temperature for about 4 hrs. Allow the reaction mixture to cool to RT. Add acetic acid (2.7 mL, 45.4 mmoles) and warm to 40° C. Add water (40 mL) slowly over 2.5 h to provide a thick, white slurry. Continue heating for an additional 1.5 h and then allow the slurry to cool to RT. Collect the solid by filtration and sequentially wash the solid with ethanol:water (20 mL, 1:1), water (20 mL). Suspend the solid in water (70 mL); collect the solid via filtration; then wash the solid with water (2×20 mL). Repeat to the water slurry two additional times. Collect the resulting solid and dry at 60° C. to provide the titled compound as a white solid (6.1 g).

Example 7

Crystallization of Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid Hydrate Charge a scintillation vial with BCCA (60 mg) and add 1.5 ml of MeOH. Heat the clear solution to about 45° C. Add 1.5 molar equivalence of formic acid in 100 µL of water to form a white suspension. Add 0.5 mL MeOH to the white suspension, and gently heat to about 55° C. After several hours, cool the suspension to RT; and collect the white crystalline solid by vacuum filtration; and allow the solid to air dry. Analysis of this crystalline solid by solution NMR does not reveal any formic acid solvent present. The crystalline form can be further characterized by differential thermal/thermogravimetric analysis, which reveals that the crystalline form has a volatile content percentage loss of 2.6 from 38 to 133° C., which was determined to be water by TGA-MS, and has an onset event at 81° C.

Differential Thermal/Thermogravimetric Analyses

Differential thermal/thermogravimetric analyses are carried out on a Mettler Toledo DTA and TGA unit (Models TGA/SDTA 851). Samples are heated in sealed aluminum pans with a pinhole from 25 to 300-350° C. at 10° C./min with a nitrogen purge of 50 mL/min. The TGA temperature is calibrated with Indium/Aluminum standard, MP=156.6 and 660.3° C. The weight calibration is performed with manufacturer-supplied standards and verified against sodium citrate dihydrate desolvation.

XRD Spectrograph Analysis

The XRD spectrum was collected using a Bruker-AXS D4 Endeavor X-ray diffractometer utilizing a CuK source (λ=1.54056, Power: 40 kV, 50 mA) and a Vantec detector. Data collected over a range of 4-40 degrees 2θ with a stepsize of 0.009 degrees 2θ and a time per step of 0.5 seconds. Method: USP 29 <941>, displacement error correction was done using the 8.853 degrees or 17.759 degrees 2θ peak of the internal standard.

A listing of the major 20 peaks is provided in Table 1 below:

TABLE 1

| Angle: (2-θ °) | Intensity I/I$_0$ (%) | d Value (Angstrom) |
|---|---|---|
| 7.5 | 28.7 | 11.83 |
| 9.2 | 20.6 | 9.62 |
| 10.7 | 50.7 | 8.28 |
| 10.9 | 24.5 | 8.09 |
| 11.3 | 43.5 | 7.82 |
| 12.2 | 13.8 | 7.26 |
| 12.4 | 21.9 | 7.11 |
| 12.7 | 17.6 | 6.95 |
| 13.8 | 49.8 | 6.41 |

TABLE 1-continued

| Angle: (2-θ °) | Intensity I/I$_0$ (%) | d Value (Angstrom) |
|---|---|---|
| 15.0 | 64.7 | 5.90 |
| 15.5 | 100.0 | 5.70 |
| 16.5 | 22.6 | 5.37 |
| 16.7 | 25.7 | 5.32 |
| 17.7 | 33.1 | 5.00 |
| 18.5 | 32.9 | 4.80 |
| 18.7 | 33.2 | 4.75 |
| 19.0 | 28.0 | 4.66 |
| 19.5 | 54.5 | 4.54 |
| 20.5 | 12.8 | 4.32 |
| 20.7 | 13.6 | 4.30 |
| 21.0 | 23.7 | 4.23 |
| 21.7 | 18.8 | 4.09 |
| 21.8 | 15.1 | 4.08 |
| 22.1 | 23.7 | 4.02 |
| 22.7 | 12.4 | 3.92 |
| 25.1 | 32.6 | 3.55 |
| 26.9 | 10.6 | 3.31 |

It is well known in the crystallography art that, for any given crystal form, the relative intensities of the diffraction peaks may vary due to preferred orientation resulting from factors such as crystal morphology. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also known in the crystallography art that, for any given crystal form, the angular peak positions may vary slightly. For example, peak positions can shift due to a variation in the temperature at which a sample is analyzed, sample displacement, or the presence or absence of an internal standard. In the present case, a peak position variability of ±0.2° in 2θ will take into account these potential variations without hindering the unequivocal identification of the crystalline salts of the present invention.

A well-known and accepted method for searching crystal forms in the literature is the "Fink" method. The Fink method uses the four most intense lines for the initial search followed by the next four most intense lines.

Example 8

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid Methanol Solvate Suspend BCCA (4 grams) in 4 mL of methanol and heat to reflux. Add approximately 50 mL more methanol to produce a slight suspension. Cool the mixture to room temperature and hold for a day. Isolate the solid product by vacuum filtration and store in a methanol chamber to protect this metastable crystal form from moisture.

Example 9

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid Ethanol Solvate Suspend BCCA (3 gram) in 10 mL of ethanol for a few hours. Isolate the solid product by vacuum filtration and store in an ethanol chamber to protect this metastable crystal form from moisture.

Example 10

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid Formic Acid Solvate Dissolve BCCA in 7 mL of isopropanol. Add formic acid (3 mL) to the solution. Add water to cloud point (4 mL) at room temperature. Heat the suspension to 70° C. for 6 hours followed by cooling to room temperature. Isolate the solid product by vacuum filtration and air-dry. The XRD spectrum was collected as described in Example 7. Table 2 below lists the peaks obtained from the XRD spectrum.

TABLE 2

| Angle: (2-θ °) | Intensity I/I$_0$ (%) | d value (Angstrom) |
|---|---|---|
| 6.3 | 3.5 | 13.94968 |
| 9.3 | 17.7 | 9.51672 |
| 9.9 | 16.5 | 8.88574 |
| 10.7 | 8.5 | 8.26542 |
| 11.1 | 16 | 7.96996 |
| 11.5 | 4.9 | 7.66788 |
| 12.2 | 11.6 | 7.26781 |
| 12.7 | 5.7 | 6.9724 |
| 13.0 | 30.5 | 6.79403 |
| 13.9 | 32.7 | 6.34956 |
| 14.4 | 1.3 | 6.15366 |
| 14.9 | 13.2 | 5.93156 |
| 15.4 | 94.8 | 5.73681 |
| 15.7 | 51.8 | 5.64135 |
| 16.4 | 33.8 | 5.40178 |
| 16.9 | 69.1 | 5.25235 |
| 18.2 | 62.3 | 4.86504 |
| 18.6 | 100 | 4.76188 |
| 19.5 | 39.9 | 4.54984 |
| 19.9 | 22.2 | 4.46884 |
| 20.3 | 84 | 4.37738 |
| 20.8 | 34.3 | 4.25735 |
| 21.2 | 25.3 | 4.18 |
| 21.8 | 28.9 | 4.0714 |
| 22.1 | 21.7 | 4.02645 |
| 22.3 | 12.9 | 3.98942 |
| 22.8 | 42.2 | 3.89217 |
| 23.5 | 1.6 | 3.78509 |
| 23.9 | 10.5 | 3.72471 |
| 24.4 | 26.9 | 3.64202 |
| 25.7 | 54.3 | 3.46701 |
| 26.3 | 13.3 | 3.38649 |
| 26.9 | 28.1 | 3.31071 |
| 27.4 | 3 | 3.25174 |
| 27.7 | 7.9 | 3.21293 |
| 28.1 | 18.9 | 3.17584 |
| 28.8 | 0.3 | 3.09618 |
| 29.3 | 4.7 | 3.04676 |
| 29.6 | 9.5 | 3.01312 |
| 30.1 | 9.9 | 2.97021 |
| 30.5 | 2.2 | 2.92929 |
| 31.1 | 17.2 | 2.87149 |
| 31.5 | 6 | 2.83836 |
| 32.1 | 3 | 2.78284 |
| 32.8 | 1.4 | 2.725 |
| 33.3 | 8.4 | 2.68817 |
| 33.7 | 2.4 | 2.65549 |
| 34.1 | 1.9 | 2.62877 |
| 35.0 | 3.6 | 2.56476 |
| 35.2 | 5.2 | 2.54651 |
| 36.2 | 8.8 | 2.4816 |
| 37.1 | 5.3 | 2.41971 |
| 37.6 | 4.4 | 2.38904 |
| 38.1 | 1 | 2.35966 |
| 38.5 | 1.8 | 2.33689 |
| 38.8 | 4.4 | 2.31826 |
| 39.1 | 6.1 | 2.30101 |

TABLE 2-continued

| Angle: (2-θ °) | Intensity I/I$_0$ (%) | d value (Angstrom) |
|---|---|---|
| 39.5 | 0.5 | 2.27748 |
| 25.5 | 47.3 | 3.49258 |

Example 11

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid Acetic Acid Solvate Suspend Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid (1.5 grams) in 10 mL of heptane. Heat the suspension to 50° C. Add 1 mL of acetic acid, and the suspension becomes clear. Add 10 ml more of heptane and cool to room temperature. Isolate the solid product by vacuum filtration and air-dry. The XRD spectrum was collected as described in Example 7. Table 3 below lists the peaks obtained from the XRD spectrum.

TABLE 3

| Angle: (2-θ °) | Intensity I/I$_0$ (%) | d value (Angstrom) |
|---|---|---|
| 6.1 | 13.9 | 14.44535 |
| 7.4 | 5.5 | 11.91759 |
| 7.7 | 3.9 | 11.43266 |
| 9.1 | 36.1 | 9.71543 |
| 9.5 | 7.2 | 9.26358 |
| 10.3 | 7.2 | 8.56123 |
| 10.6 | 9.9 | 8.35606 |
| 11.0 | 49.7 | 8.03505 |
| 11.3 | 9.4 | 7.85127 |
| 12.0 | 17.1 | 7.34832 |
| 12.3 | 8.7 | 7.15849 |
| 12.6 | 11.4 | 6.99570 |
| 12.9 | 69.1 | 6.84536 |
| 13.8 | 59.9 | 6.42263 |
| 14.1 | 12.0 | 6.28300 |
| 14.6 | 18.4 | 6.04828 |
| 14.9 | 42.7 | 5.93036 |
| 15.1 | 64.5 | 5.85341 |
| 15.6 | 47.5 | 5.68615 |
| 16.1 | 25.3 | 5.48924 |
| 16.4 | 60.8 | 5.40742 |
| 16.6 | 15.5 | 5.33346 |
| 17.8 | 62.9 | 4.99156 |
| 18.4 | 100.0 | 4.82513 |
| 18.6 | 25.0 | 4.75791 |
| 19.0 | 22.8 | 4.67246 |
| 19.4 | 70.3 | 4.57246 |
| 19.6 | 36.3 | 4.51720 |
| 20.1 | 54.0 | 4.40286 |
| 20.8 | 68.0 | 4.26852 |
| 21.1 | 42.1 | 4.19902 |
| 21.4 | 17.2 | 4.15565 |
| 21.7 | 52.5 | 4.08624 |
| 22.2 | 31.5 | 3.99752 |
| 22.7 | 40.3 | 3.90975 |
| 23.3 | 14.1 | 3.81432 |
| 24.2 | 23.9 | 3.66935 |
| 24.9 | 33.2 | 3.56724 |
| 25.5 | 40.1 | 3.49233 |
| 25.8 | 10.4 | 3.44753 |
| 26.2 | 19.8 | 3.39235 |
| 26.6 | 29.0 | 3.34914 |
| 26.9 | 8.1 | 3.31407 |

TABLE 3-continued

| Angle: (2-θ °) | Intensity I/I₀ (%) | d value (Angstrom) |
|---|---|---|
| 27.6 | 9.9 | 3.23104 |
| 27.9 | 11.3 | 3.19103 |
| 28.9 | 8.0 | 3.08812 |
| 29.6 | 5.4 | 3.01802 |
| 30.2 | 5.4 | 2.95795 |
| 30.6 | 4.3 | 2.91735 |
| 31.3 | 5.5 | 2.85866 |
| 32.1 | 6.1 | 2.78825 |
| 32.7 | 5.2 | 2.73423 |
| 33.0 | 7.2 | 2.71300 |
| 33.9 | 5.1 | 2.63900 |
| 34.3 | 3.5 | 2.61366 |
| 35.0 | 7.1 | 2.56146 |
| 35.7 | 3.2 | 2.51192 |
| 36.1 | 3.9 | 2.48827 |
| 36.3 | 3.8 | 2.47610 |
| 36.7 | 3.4 | 2.44761 |
| 37.0 | 4.4 | 2.42813 |
| 37.3 | 3.3 | 2.40594 |
| 37.7 | 4.2 | 2.38107 |
| 38.5 | 4.6 | 2.33422 |
| 39.3 | 4.1 | 2.28755 |

Example 12

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid sodium salt Add to a 500 mL bottle Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid hydrate (20.16 g) ethanol SDA 3A (200.94 mL). Stir using a magnetic stir bar and slowly add 1 N sodium hydroxide (31.95 g). This is a clear solution.

Spray drying: Use a spray dryer (Niro SD Micro Spray Dryer) and use a drying gas flow rate to 32.5 kg/hr, 2.8 bar, atomization gas flow rate to 2.0 kg/hr, 0.3 bar, and inlet temperature (automatic control) 115° C. Once inlet temperature is at 115° C. and outlet temp had stabilized (109° C.), start flow of 83:17 (w/w) ethanol:water to atomizer. At a pump setting of 3.0, no drops hitting walls/outlet of chamber. Allow system to reach thermal equilibrium-outlet=104° C. Switch from ethanol:water (at room temp) to drying sample in a solution of ethanol/water. After spray drying, results in 13.51 g.

Example 13

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid magnesium salt Dissolve Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid sodium salt (2 grams) in 5 mL of methanol. Dissolve magnesium acetate (335 mg) in 2θ mL of water. Add the magnesium acetate solution drop wise at room temperature with aggressive stirring and follow by heating to 65° C. Precipitation occurs. At the elevated temperature, add an additional 10 mL of water. Cool the suspension to room temperature and isolate the solid product by vacuum filtration and rinse with water. Dry the product in a vacuum oven at room temperature.

The calcium and zinc salts of BCCA may be prepared by an analogous procedure to that for the preparation of the BCCA magnesium salt. The potassium salt may be prepared by an analogous procedure to that for the preparation of the BCCA sodium salt.

Example 14

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid tert-butylamine isopropyl alcohol (1:1:1) solvate Set up a 1 L three neck round bottom flask fitted with a mechanical stirrer, temperature controller, addition funnel, and heating mantle. Suspend Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid hydrate (50 g) in heptane (500 mL). Heat the slurry to 69.1° C. and add tert-butylamine (5.57 g) as a solution in isopropyl alcohol (70 mL) and rinse in with 5 mL additional isopropyl alcohol. A solution forms immediately upon addition. During addition, temperature drops to 63° C. but heats back up to 69° C. once addition is complete. Seed with a spatula tip of Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid tert-butylamine. A suspension begins to form—continue stirring at 69° C. Begin cooling the reaction to 55° C. In about an hour, a thick slurry forms. Continue cooling to 45° C. In about an hour, bring temperature of slurry down to 35° C. In about 2 hours, remove heat source and allow to cool to ambient temperature. In about 3 hours, filter the slurry (temperature is now 21° C.) and rinse with 100 mL of heptane. Dry using a vacuum for about an 1.5 hours. Dry over the weekend in vacuo at 33° C. This results in 55.9 g. The XRD spectrum was collected as described in Example 7. Table 4 below lists the peaks obtained from the XRD spectrum.

TABLE 4

| Angle (2-θ °) | Intensity I/I₀ (%) | d Value (Angstrom) |
|---|---|---|
| 5.6 | 44.1 | 15.66139 |
| 8.0 | 25.8 | 11.06129 |
| 8.9 | 14.1 | 9.90002 |
| 10.9 | 7.3 | 8.08475 |
| 11.3 | 49.2 | 7.84359 |
| 11.5 | 2.6 | 7.67967 |
| 12.3 | 1.9 | 7.19816 |
| 12.6 | 50.1 | 7.01593 |
| 12.8 | 2.2 | 6.88749 |
| 13.5 | 5.5 | 6.52796 |
| 14.4 | 9.4 | 6.14491 |
| 15.2 | 3.5 | 5.81628 |
| 15.7 | 1.7 | 5.62539 |
| 16.0 | 3.0 | 5.54451 |
| 16.2 | 6.6 | 5.45377 |
| 16.5 | 9.5 | 5.38135 |
| 16.9 | 1.4 | 5.22767 |
| 17.3 | 1.7 | 5.11298 |
| 17.9 | 100.0 | 4.95461 |
| 19.0 | 2.6 | 4.67047 |
| 19.4 | 9.2 | 4.56973 |

TABLE 4-continued

| Angle (2-θ °) | Intensity I/I₀ (%) | d Value (Angstrom) |
|---|---|---|
| 19.8 | 18.4 | 4.47579 |
| 20.0 | 4.3 | 4.43314 |
| 20.4 | 31.4 | 4.34849 |
| 20.6 | 10.7 | 4.30398 |
| 20.9 | 7.4 | 4.25624 |
| 21.2 | 2.6 | 4.18059 |
| 21.6 | 16.3 | 4.11389 |
| 22.5 | 15.6 | 3.94560 |
| 22.7 | 10.1 | 3.92057 |
| 22.9 | 4.9 | 3.88729 |
| 23.4 | 14.3 | 3.79936 |
| 24.1 | 32.8 | 3.69727 |
| 24.4 | 2.7 | 3.64309 |
| 25.4 | 17.6 | 3.50430 |
| 25.7 | 2.8 | 3.46139 |
| 26.2 | 2.2 | 3.40048 |
| 26.5 | 3.9 | 3.36314 |
| 27.4 | 1.7 | 3.25294 |
| 27.7 | 3.4 | 3.21470 |
| 28.4 | 2.2 | 3.13589 |
| 28.8 | 1.9 | 3.09670 |
| 29.0 | 10.9 | 3.07330 |
| 30.0 | 1.7 | 2.97494 |
| 30.3 | 2.2 | 2.94722 |
| 30.7 | 3.6 | 2.91172 |
| 31.1 | 2.7 | 2.87130 |
| 31.5 | 1.8 | 2.83951 |
| 32.0 | 1.6 | 2.79091 |
| 32.3 | 1.8 | 2.77270 |
| 32.5 | 3.5 | 2.74970 |
| 33.3 | 2.7 | 2.69165 |
| 34.2 | 2.5 | 2.62286 |
| 34.5 | 1.7 | 2.59477 |
| 34.8 | 1.6 | 2.57771 |
| 35.9 | 1.4 | 2.49750 |
| 36.2 | 2.0 | 2.48053 |
| 36.6 | 2.7 | 2.45071 |
| 37.1 | 1.2 | 2.42094 |
| 37.3 | 1.7 | 2.40638 |
| 37.7 | 1.2 | 2.38295 |
| 38.0 | 1.5 | 2.36721 |
| 38.3 | 2.0 | 2.34975 |
| 38.8 | 2.8 | 2.31827 |
| 40.0 | 1.4 | 2.25835 |

Example 15

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid hemi tert-butylamine salt hemi ethanol (2:1:1) solvate in crystalline form Suspend Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid hydrate (50.5 g) in heptane (404.00 mL) with mechanical overhead stirring. Add ethanol (25.25 mL) and heat to 55° C. A solution forms. Add tert-butylamine (2.81 g) at 55° C. Seed with Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid hemi tert-butylamine hemi ethanol (2:1:1) solvate and seed persists. Maintain temperature at 50° C. A fairly thick slurry forms by within minutes with an exotherm up to 60° C. Continue to stir and cools back to 50° C. After about 5.5 hours, turn off heat and allow to cool to ambient temperature. In about 3 hours, filter, rinse flask out with portion of mother liquor, and then rinse cake with 100 mL of heptane. Dry overnight in vacuo at 45° C. 50.9 g. The XRD spectrum was collected as described in Example 7. Table 5 below lists the peaks obtained from the XRD spectrum.

TABLE 5

| Angle (2-θ °) | Intensity I/I₀ (%) | d Value (Angstrom) |
|---|---|---|
| 4.4 | 7.9 | 19.89438 |
| 5.5 | 100.0 | 15.98834 |
| 7.0 | 11.1 | 12.56184 |
| 9.0 | 68.2 | 9.80480 |
| 10.5 | 2.8 | 8.37905 |
| 11.0 | 6.7 | 8.03163 |
| 13.2 | 14.6 | 6.72015 |
| 13.6 | 15.4 | 6.51691 |
| 14.3 | 91.3 | 6.16773 |
| 14.7 | 6.5 | 6.03809 |
| 15.2 | 19.3 | 5.81709 |
| 16.4 | 7.7 | 5.38980 |
| 17.1 | 8.5 | 5.16503 |
| 17.5 | 47.8 | 5.06441 |
| 18.2 | 56.5 | 4.87353 |
| 19.4 | 42.7 | 4.58173 |
| 19.8 | 13.6 | 4.47894 |
| 20.0 | 16.8 | 4.44358 |
| 20.6 | 36.0 | 4.31170 |
| 21.3 | 4.7 | 4.16561 |
| 22.0 | 66.4 | 4.04259 |
| 22.5 | 60.2 | 3.95496 |
| 22.8 | 8.5 | 3.89683 |
| 23.6 | 10.5 | 3.76398 |
| 24.2 | 8.0 | 3.66760 |
| 24.5 | 9.1 | 3.63014 |
| 25.2 | 3.0 | 3.53057 |
| 25.5 | 11.9 | 3.48459 |
| 26.0 | 4.9 | 3.42535 |
| 26.5 | 10.1 | 3.36294 |
| 26.8 | 8.5 | 3.32729 |
| 27.4 | 7.4 | 3.24977 |
| 28.2 | 3.6 | 3.16032 |
| 29.0 | 10.2 | 3.07299 |
| 29.8 | 2.6 | 2.99108 |
| 30.3 | 1.7 | 2.94967 |
| 30.8 | 2.8 | 2.90463 |
| 31.3 | 1.8 | 2.85529 |
| 31.6 | 2.2 | 2.83127 |
| 31.9 | 2.0 | 2.80658 |
| 32.2 | 1.3 | 2.77693 |
| 32.5 | 2.1 | 2.75134 |
| 32.8 | 2.8 | 2.72867 |
| 33.1 | 2.6 | 2.70617 |
| 33.4 | 4.0 | 2.68312 |
| 33.6 | 2.1 | 2.66202 |
| 33.9 | 1.3 | 2.64016 |
| 34.3 | 2.6 | 2.61178 |
| 34.9 | 1.9 | 2.57048 |
| 35.3 | 3.5 | 2.54278 |
| 35.9 | 1.6 | 2.50187 |
| 36.2 | 1.2 | 2.47774 |
| 36.6 | 2.0 | 2.45291 |
| 37.1 | 3.7 | 2.42008 |
| 37.5 | 1.6 | 2.39905 |
| 37.9 | 2.0 | 2.37147 |
| 38.5 | 2.5 | 2.33798 |

Example 16

Trans-4-[[(5S)-5-[[[3,5-bis(trifluoromethyl)phenyl]methyl](2-methyl-2H-tetrazol-5-yl)amino]-2,3,4,5-tetrahydro-7,9-dimethyl-1H-1-benzazepin-1-yl]methyl]-cyclohexanecarboxylic acid.hydrate Step 13 of Scheme 3: Add 2 M NaOH solution (9.9 L) to Methyl-trans-4-{[(5S)-5-{[3,5-bis(trifluoromethyl)benzyl](2-methyl-2H-tetrazol-5-yl)amino}-7,9-dimethyl-2,3,4,5- tetrahydro-1H-1-benzazepin-1-yl]methyl}cyclohexanecarboxylate (12.95 kg) at room temperature and stir the reaction for 10 minutes. Stir reaction at 40° C. to 45° C. for 6 hours. Monitor the reaction by HPLC. Add acetic acid (3.75 kg) to the mixture followed by water (1.2 volumes), seed with BCCA.hydrate and stir for 2 hours at 40° C. to 45° C. Add water (2.8 volumes) to the reaction mixture and stir for 2 hours at 40° C. to 45° C. Cool the reaction mixture to room temperature, stir for 2 hours, and filter. Collect solids, wash with ethanol:H$_2$O (1:1; 2×2 volumes), and dry on the pressure filter overnight. This results in 15.87 kg of solid material for use in step 2.

Add methanol to the solid material of step 1 and stir at 65° C. to 70° C. for 2 hours to get a clear solution. Polish filter through a plate pressure filter to a secondary reactor, stir the filtrate for 2 hours at 0° C. to 5° C., filter, and dry on a pressure filter overnight. Stir the recrystallized solid in water (10 volumes) at room temperature for 2 hours, filter, and dry on a pressure filter. Dry in the oven under high vacuum at 40° C. to 45° C. to approximately 2.7 to 3.1% water by Karl Fisher analysis. This results in 11.80 kg of material.

Karl Fisher analysis=3.16%

Mass Spectrometry by ES-API in positive mode=639.30; in negative mode 637.20.

Chemical Stability

Table 6 below lists the chemical stability of BCCA free acid as well as that of selected Examples 31, 89, 153, and 175 disclosed in WO 06/002342, renumbered below as compounds 13, 14, 15, and 16, respectively. The data below demonstrates that BCCA free acid provide advantageous properties by exhibiting increased stability in aqueous acidic media significantly greater than that exhibited by compounds 13, 14, and 16. This increased acid stability for BCCA free acid is not taught and cannot be predicted considering WO 06/002342.

TABLE 6

| | | | Acid Stability | |
|---|---|---|---|---|
| | | | 0.1 N HCl 40° C.† | |
| Cpd | Structure | Name | 8 hrs | 24 hrs |
| Ex 1 | | BCCA free acid | 97.3 | 91.3 |
| 13 | | (4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-cyclohexyl)-acetic acid | 14.5 | 0 |

TABLE 6-continued

Acid Stability

| Cpd | Structure | Name | 0.1 N HCl 40° C.† | |
|---|---|---|---|---|
| | | | 8 hrs | 24 hrs |
| 14 | | (S)-4-{5-[(3,5-Bis-trifluoromethyl-benzyl)-(2-methyl-2H-tetrazol-5-yl)-amino]-7-methyl-8-trifluoromethyl-2,3,4,5-tetrahydro-benzo[b]azepin-1-ylmethyl}-benzoic acid | 52 | 13.4 |
| 15 | | (S)-(4-{5-[(3,5-Bis-trifluoromethyl-benzyl)-(2-methyl-2H-tetrazol-5-yl)-amino]-7,9-dimethyl-8-trifluoromethyl-2,3,4,5-tetrahydro-benzo[b]azepin-1-ylmethyl}-cyclohexyl)-acetic acid | 100.4 | 99.1 |
| 16 | | (S)-4-{5-[(3,5-Bis-trifluoromethyl-benzyl)-2-methyl-2H-tetrazol-5-yl)-amino]-7-methyl-8-trifluoromethyl-2,3,4,5-tetrahydro-benzo[b]azepin-1-yl}-cyclohexanecarboxylic acid | 37.8 | 13.4* |

†Percent remaining; each compound was run in separate experiment according to the procedure immediately below.
*Percent remaining after 16 hrs Sample preparations: 1) Compound Stock: 0.9 mg/mL in ACN; 2) 100 µL stock+700 µL ACN+1 mL media (0.1N HCl, 50 mM $PO_4$, pH 8, and 0.3% $H_2O_2$); 3) Place vials in heated (40° C.) autosampler, inject at 4 hour intervals for 16 or 24 hours.

Chromatography Autosampler Conditions
Column: Alltech Alltima Phenyl, 3 µm, 4.6×150 mm or Waters XTerra MS C18, 3.5 µm, 4.6×150 mm Column temperature: 50° C., Injection volume: 10 µL. Detection: UV @ 226, 254 or 266 nm (depending on compound) Flow rate: 1.5 mL/min. Mobile phase: 0.1% TFA in 50% water/50% ACN (may need to adjust % ACN to keep compound peak retention time~5 min.) final sample conc. 0.05 mg/mL; ACN content 44%.

Determination of IV and PO Pharmacokinetics of CETP Inhibitor Compounds in Male Sprague Dawley Rats for Comparison This following is to determine the pharmacokinetic parameters, including oral bioavailability, following a single 1 mg/kg intravenous bolus or a 3 mg/kg oral dose administration of the compound to male Sprague Dawley rats (n=4) in a crossover study design. The intravenous vehicle is 20% solutol microemulsion/80% deionized water. The oral vehicle is povidone USP 10%/SLS 0.5%/QS deionized water. In the intravenous arm, blood samples are collected at 0.08, 0.25, 0.5, 1, 2, 5, 8, 12, and 24 hours post-dose. In the oral arm, blood samples are collected at 0, 0.25, 0.5, 1, 2, 5, 8, 12, and 24 hours post-dose. Plasma is obtained by centrifugation, placed on ice, and frozen until samples are shipped on dry ice to Bioanalytical Systems, Inc. (BASi; West Lafayette, Ind.) for bioanalytical analysis. Concentrations of BCCA are determined by LC/MS/MS and pharmacokinetic parameters are calculated using a validated software program (Watson, Version 7.1). Other vehicles can be used to evaluate the bioavailability of BCCA including: 1% w/v sodium carboxymethyl cellulose, 0.25% w/v polysorbate 80 (Tween 80) and 0.05% 0.05% Dow Corning Antifoam 1510-US in purified water or; 1% w/v sodium carboxymethyl cellulose, 0.5% w/v sodium laurate sulfate, and 0.05% 0.05% Dow Corning Antifoam 1510-US in purified water in purified water each used either with or without sonication to facilitate dissolution of the compounds.

The data below in Table 7 demonstrates that BCCA free acid provides advantages exhibiting greater than 4 times the bioavailability of that exhibited by compound 15 (Example 153 in WO 06/002342). This increased bioavailability is not taught and cannot be predicted considering WO 06/002342.

TABLE 7

Pharmacokinetic (PK) data

| Cpd No. | Cmax p.o. (ng/mL) ± sd | Tmax p.o. (hr) ± sd | F % (AUC Extrap.) ± sd † |
|---|---|---|---|
| BCCA free acid | 208 ± 41 | 3.5 ± 1.7 | 38 ± 4 |
| 15 | 85 ± 43 | 5.0 ± 0 | 8 ± 3 |

† 3 mg/kg PO (2 ml/kg dose volume), 1 mg/kg IV (1 mL/kg dose volume)

Assays

The following assay protocols and result(s) thereof demonstrating the utility and efficacy of the compound and/or methods of the current invention are given for the purpose of illustration and are not meant to be limiting in any way.

In Vitro CETP Inhibitor Assay: SPA ASSAY

An in vitro Scintillation Proximity Assay (SPA) has been used to evaluate the ability of compounds of this invention to inhibit the transfer of radiolabeled cholesterol esters between HDL and LDL. This assay monitors the inhibition of the transfer of [$^3$H]cholesterol esters from HDL (Amersham) to biotinylated LDL (Amersham) by a CETP source. The CETP source for this assay can be produced by AV-12 cells that have been created to express human CETP. The radiolabeled cholesterol ester is transferred in a HEPES-NaCl based buffer, after thirty minutes incubation the reaction is stopped and the biotinylated LDL is bound to streptavidin/scintillant coated SPA beads (Amersham). The radioactive signal is measured in a Packard 96-well scintillation TopCounter with window settings fully open. A decrease in radioactive signal from the LDL relative to a standard indicates the ability of compounds to inhibit the activity of CETP.

Alternatively, other CETP sources can be used to mediate the transfer of radiolabeled cholesterol ester in this assay. For example, endogenous CETP from human plasma, CETP from mice that express human CETP, and endogenous CETP from hamsters can be used as the CETP source in this assay.

Buffers other than HEPES-NaCl based buffer can be used in this assay, for example, human plasma, mouse plasma or a Tris-buffer that is high in albumin may be used.

It will be understood by those skilled in the art that other sources of radioactivity may be used to track the CETP activity in this assay.

Additionally, radio labeled-LDL may be used in this assay.

The activity of BCCA to inhibit transfer of radiolabeled cholesterol esters between HDL and LDL according to this assay is listed below in Table 8.

Activity of compounds of this invention in vivo can be evaluated by comparing the level of elevation of HDL cholesterol relative to a control by a given amount of a compound in a CETP-containing animal species. The test compounds are administered as described above for the in vivo assay of CETP activity. At various times after dosing, ranging from 4 h to 24 h, blood is obtained. The blood is allowed to clot, and serum is obtained from the clotted blood by centrifugation. The HDL cholesterol levels in the serum can be determined by known procedures using HDL-C plus reagents (Roche/Hitachi, Indianapolis, Ind.) with a clinical chemistry analyzer (Roche/Hitachi, Indianapolis, Ind.). Additional serum lipids can be analyzed by enzymatic methods. Lipids in the VLDL, LDL and HDL fractions are analyzed by enzymatic methods after precipitation or size exclusion chromatography. An example of the elevation of HDL cholesterol levels at 8 hr after administration of amorphous BCCA are summarized below in Table 8.

TABLE 8

| Cpd No. | % CETP Inhib 8 hr† | % HDL cholesterol increase at 8 hr† |
|---|---|---|
| BCCA | 98.6 | 129.7. |

†79.5% corn oil, 20% oleic acid, 0.5% Lubrafil, 30 mpk dose, female or male CETP and Apo A1 heterozygote mice (Taconic).

Method of Treatment

As used herein, the term "effective amount" means an amount of compound of the present invention, i.e., amorphous BCCA, BCCA.solvate, BCCA salt.solvate and/or BCCA.hydrate in crystalline form or a combination thereof, which is capable of alleviating the symptoms of the various pathological conditions attributed to cardiovascular diseases. Examples of cardiovascular diseases include but are not limited to: coronary heart disease, strokes, arthrosclerosis, dyslipidemia, low high density lipoprotein (HDL), hypercholesterolemia, and peripheral vascular disease.

A specific dose of a compound administered according to this invention can be determined by the particular circumstances surrounding the case including, for example, but not limited to: the compound administered, the route of administration, the state of being of the patient, and the pathological condition being treated as determined by the attending physician. A typical daily dose will contain from about 10 mg to about 750 mg/day of a compound of the present invention. Preferred daily doses generally will be from about 30 mg to about 600 mg/day, still more preferable from about 50 and to about 300 mg/day.

The compounds of this invention may be administered by a variety of routes. Preferably the compounds of the invention are formulated into tablets, solid or gel filled capsules, powders, solutions or suspensions.

Pharmaceutical formulations of the present invention may be prepared by procedures known in the art using well-known and readily available ingredients. The term "pharmaceutically acceptable" as used herein refers to one or more carriers, diluents, excipients and salts are compatible with the other ingredients of the formulation and not deleterious to the recipient thereof. Pharmaceutical compositions and processes for their preparation are known in the art and examples can be found in Remington, "The Science and Practice of Pharmacy" (A. Gennaro, et al. eds. 19$^{th}$ ed. Mack Publishing Co.) Non-limiting examples of pharmaceutically acceptable carriers, excipients, and diluents are suitable for such formulations include the following: starch, sugars, mannitol, and silica derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium, and magnesium stearate, and solid polyethyl glycols. In one form, the pharmaceutical formulation includes mannitol, sodium lauryl sulfate, colloidal silicon dioxide, sodium croscarmellos, microcrystalline cellulose and magnesium stearate, and can include the drug substance, BCCA, BCCA free acid, BCCA hydrate or BCCA hydrate in crystalline form in a range of between about 2 and about 21% w/w.

Thus, another aspect of the present invention is a pharmaceutically acceptable salt of a compound provided by this invention. Examples of pharmaceutically salts can be found in S. M. Berge, et al., "Pharmaceutical Salts," *J. Phar. Sci.*, 66: 1-19 (1977) and "A Handbook of Pharmaceutical Salts Properties, Selection, and Use", Wermuth, C. G. and Stahl, P. H. (eds.) Verlag Helvtica Chimica Acta, 2002, which are incorporated herein.

What is claimed is:
1. A compound having a structure illustrated below:

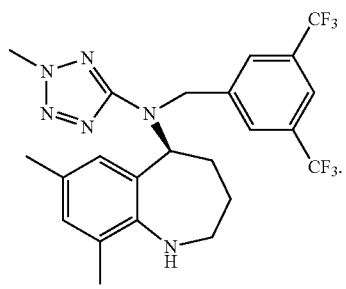

III

* * * * *

UNITED STATES PATENT AND TRADEMARK OFFICE
CERTIFICATE OF CORRECTION

PATENT NO. : 8,329,688 B2
APPLICATION NO. : 12/824355
DATED : December 11, 2012
INVENTOR(S) : Xinchao Chen It is certified that error appears in the above-identified patent and that said Letters Patent is hereby corrected as shown below:

In the issued patent, please note the following corrections:

On the first page, Column 2 (Other Publication), line 4, please delete "Cycloadditionwith" and insert --Cycloaddition with--, therefor.

On the first page, Column 2 (Other Publication), line 9, please delete "Entantioselective" and insert --Enantioselective--, therefor.

On the first page, Column 2 (Other Publication), line 14, please delete "Additionof" and insert --Addition of--, therefor.

On the first page, Column 2 (Other Publication), line 15, please delete "Italinan," and insert --Italiana,--, therefor.

In column 1, line 9, please delete "60/221,708" and insert --61/221,708--, therefor.

Signed and Sealed this
Twelfth Day of February, 2013

Teresa Stanek Rea
*Acting Director of the United States Patent and Trademark Office*